United States Patent
Onishi

(10) Patent No.: US 9,339,549 B2
(45) Date of Patent: May 17, 2016

(54) CATIONIC GRAFT-COPOLYMER FOR DRUG DELIVERY SYSTEM

(71) Applicant: Yasuhiko Onishi, Seto (JP)

(72) Inventor: Yasuhiko Onishi, Seto (JP)

( * ) Notice: Subject to any disclaimer, the term of this patent is extended or adjusted under 35 U.S.C. 154(b) by 0 days.

(21) Appl. No.: 14/378,974

(22) PCT Filed: Feb. 21, 2013

(86) PCT No.: PCT/JP2013/055602
§ 371 (c)(1),
(2) Date: Aug. 15, 2014

(87) PCT Pub. No.: WO2013/125730
PCT Pub. Date: Aug. 29, 2013

(65) Prior Publication Data
US 2015/0072938 A1   Mar. 12, 2015

(51) Int. Cl.
*A61K 31/337* (2006.01)
*A61K 38/13* (2006.01)
*A61K 47/36* (2006.01)
*A61K 47/32* (2006.01)
*A61K 47/48* (2006.01)

(52) U.S. Cl.
CPC .............. *A61K 47/36* (2013.01); *A61K 31/337* (2013.01); *A61K 38/13* (2013.01); *A61K 47/32* (2013.01); *A61K 47/4823* (2013.01)

(58) Field of Classification Search
CPC ..... A61K 31/337; A61K 38/13; A61K 47/32; A61K 47/36; A61K 47/4823; C08L 51/02; C08L 51/00; A61L 27/16; C08B 37/0021
See application file for complete search history.

(56) References Cited

U.S. PATENT DOCUMENTS

| | | | | |
|---|---|---|---|---|
| 4,816,540 A | * | 3/1989 | Onishi | C08F 251/00 527/300 |
| 2005/0287110 A1 | * | 12/2005 | Onishi | C08F 251/00 424/78.3 |
| 2006/0013854 A1 | * | 1/2006 | Strickler et al. | A61L 29/041 424/423 |

FOREIGN PATENT DOCUMENTS

| | | |
|---|---|---|
| EP | 1583782 A2 | 10/2005 |
| JP | 2005-102681 A | 4/2005 |
| WO | WO 2004/065440 A2 | 8/2004 |

OTHER PUBLICATIONS

Supramolecular Facilities to Melanoma Cells B16F10 with Nanoparticles of a DEAE-Dextran-MMA Copolymer-Paclitaxel Complex, Eshita et al. Journal Nanomed Nanotechol, 2012.
Supramolecular Targeting of B16F10 Melanoma Cells with Nanoparticles Consisting of a DEAE-Dextran-MMA Copolymer-Paclitaxel Complex In vivo and In vitro, Eshita et al.Journal Nanomed Biotherapeut Discov 2012.
International Search Report, Jul. 24, 2013, from International Phase of the instant application.

* cited by examiner

*Primary Examiner* — Anna Falkowitz
(74) *Attorney, Agent, or Firm* — Luoh J. Wu; Continent Patent Office LLP

(57) ABSTRACT

A cationic graft-copolymer for a drug delivery system comprising a unit derived from a having a hydroxyl groups, namely, a cationic polysaccharide of the following formula (1) $(C_6H_7O_2(OH)_{3-a}(OX)_a)_x H_2O$ (1) and a unit derived from a polymerizable olefin compound of the following formula (2) (a, x, X, $R_4$, $R_5$, $R_6$, and $R_7$ are defined in claim 1-8); a process for preparing the same and a transfection reagent made therefrom.

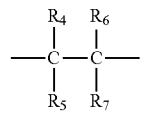

(2)

10 Claims, 3 Drawing Sheets

CATIONIC GRAFT-COPOLYMER FOR DRUG DELIVERY SYSTEM

TECHNICAL FIELD

This invention relates to cationic copolymers and its supramolecular compound for drug delivery system that were obtained by graft-polymerizing a vinyl monomer onto a cationic derivative of a water-soluble linear polymer having hydroxyl groups. Thus, the latex polymerization products which are useful as supramolecular system of delivery materials for anticancer agent can be produced. The supramolecule refers to a compound, the simple substance which plural molecules are organized by combination (including coordinate bond, the hydrogen bonding or hydrophobic bonding) except the covalent bond and comparative weak interaction, and self-gathered.

BACKGROUND ART

Paclitaxel by the extract of the bark of the Pacific yew or docetaxel by the extract of the needle leave of the European yew are useful the anticancer agents and it is named generally with a taxane-based anticancer agent. The action mechanism binds to the microtubule and brings microtubular polymerization promotion, stabilization, and it is thought that it inhibits cell division. These taxane-based anticancer agents are used for cancer treatment widely, and the high effectiveness for many cancer tumors such as non-small cell lung cancer, breast cancer etc. have been already confirmed. However, as toxic (a side effect) of the taxane-based anticancer agent, leucopenia, neutropenia, peripheral neuropathy, nausea vomiting are reported, and there is usually individual difference of 5-10 times with the drug blood concentration of the taxane-based anticancer agent again, and the serious toxic appearance with the rise in blood paclitaxel density is reported to the observed case.

There is also an issue of bias due to individual differences in pharmacokinetics. It is shown paclitaxel is a substrate of P-glycoprotein (MDR1/ABCB1) which is one of the transporter drugs, and has been reported that paclitaxel also are metabolized by CYP2C8, CYP3A4 primarily receive. On the other hand, docetaxel metabolism is by CYP3A4. Therefore, there is a possibility that caused by genetic polymorphisms of drug metabolizing enzymes and drug transporters of these individual differences in pharmacokinetics.

In addition, it is also seen the relatively high incidence of allergic side-effects in its additive and it is estimated many allergic side-effects that these drugs cause. Supramolecular complex by taxane anticancer agent of the present invention may have a substrate selectivity to reach a solution to these as artificial enzymes.

Concepts, as long-lasting effect by having gradually released from the drug formulation, proposed in 1968 by Argentina of the United States company (now Johnson & Johnson), are a drug delivery systems that is (DDS). Been studied until today, the use of anticancer drugs have been actively studied in particular.

The reason for this is that the expansion of the various benefits of convenience such as drug suppression of side-effects of powerful anti-cancer agents and the enhancement of drug efficacy exist by DDS. For example, the anticancer drug paclitaxel (Taxol) has been using what was dissolved in anhydrous ethanol and Cremophor EL the like for non-water soluble.

Solubilization of Taxol, by immobilized on the L-glutamic acid and by DDS such as albumin and dextrin, are known. In a drug delivery system (DDS), the diameter of a particle is enlarged by the balance of both water solubility and liposolubility or the molecular weight etc., thus the EPR effect and the RES control effect become possible. By the EPR effect, a new blood vessel of the tumor is penetrated by particle of size 10-200 nm, and the medicine piles up the tumor tissue. Particles of not less than 400 nm as a foreign substance are eliminated by phagocyte action by the Kupffer cell of liver, or the cell of the macrophage system of the adrenal gland in RES control. Since it is decomposed by drug metabolism in liver, a thing of 5 nm or less is excreted by filtration by the glomerulus of the kidney.

Thus, it is possible to maintain concentration of drug in the living body by using the optimal diameter of a particle for a long period of time.

Such a method that improves the convenience of the drug is called as pro-drugging, but there are problems whether there is possibility of the autoclave sterilization in DDS for the safety. A positive electric charge in DDS for the cancer cell surface of the negative electrostatic charge is needed so that it is busy in endocytosis in a cancer cell more efficiently.

On the other hand, it was produced latex polymerization products as immunoassay materials conventionally, but all most are emulsion-polymerized in solution of surfactant, and a thing of soap-less not to exist of the surfactant is expected. This is because an existing surfactant influences the action as the latex diagnostic agent in a water solution.

Therefore, the present invention provides a novel graft-copolymer that is composed of a cationic derivative of a water-soluble linear polymer and an olefin compound monomer.

The present invention also provides a method of graft-polymerizing an olefin compound monomer onto a cationic derivative of a water-soluble linear polymer having a hydroxyl group in water using ceric ammonium nitrate to obtain a stable and soapless latex of the graft-copolymer.

This is used for antibody adsorption latex as diagnostic agent. This technique to produce latex of soap-less is thought important to form the supramolecular compound which might have substrate selectivity as an artificial enzyme. Thus, I could produce the latex polymerization products which were useful as drug delivery (DDS) materials.

The invention of U.S. Pat. No. 4,816,540 provides a novel graft-copolymer that is composed of a cationic derivative of a water-soluble linear polymer and an olefin compound monomer.

The invention described in U.S. Pat. No. 4,816,540 also provides a method of graft-polymerizing an olefin compound monomer onto a cationic derivative of a water-soluble linear polymer in water using ceric ammonium nitrate to obtain a stable and soap-less latex of the graft-copolymer.

Namely, the obtained latex sensitized with an antibody or an antigen is agglutinated using antigen or antibody, and it can be confirmed rapidly whether the antigen or the antibody is present. The latex used for the L.A. (Latex Agglutination) test is typically a pure, stable and soap-less substance and is also very effective as a non-viral gene delivery vector.

It is shown in U.S. Pat. No. 3,989,656 that a dextran-alkyl methacrylate graft composition is obtained by polymerizing an olefin compound monomer onto a water-soluble linear polymer, such as dextran, in water using ceric ammonium nitrate.

The present invention provides a novel graft-copolymer for drug delivery system (DDS) that is composed of a cationic derivative of a water-soluble linear polymer and an olefin compound monomer.

The present invention also provides a method of graft-polymerizing an olefin compound monomer onto a cationic derivative of a water-soluble linear polymer in water using ceric ammonium nitrate to obtain a stable and soap-less latex of the graft-copolymer, which is very effective as drug delivery system (DDS).

CITATION LIST

Patent Literature

[PTL 1]
JP,2126650,B
[PTL 2]
JP,2006-517594,A
[PTL 3]
JP,2001-226294,A
[PTL 4]
JP,2005-336402,A
[PTL 5]
JP,2007-023023,A

DISCLOSURE OF INVENTION

Technical Problem

The purpose of this invention is not only the restraint of the side effect of simple drug delivery system and expansion of the convenience of the drug, but also the possibility to have substrate selectivity as an enzyme artificially and the reinforcement of the efficacy of the supramolecular anticancer agent by fixing the Multi-drug Resistance conquest agent, a cancer target material or a chemotherapy fortifier to an anticancer agent using the immobilization method newly more. Control of balance between the fat solubility and the water solubility, and molecular weight is difficult and, in drug delivery system (DDS) put to practical use, most have a problem with safety such as the heating sterilization now.

Furthermore, there are problems such as the possibility of the autoclave sterilization to DDS for the safety and a positive electric charge for the cancer cell surface of the negative electrostatic charge in a cancer cell for efficiently.

Solution to Problem

We offer a new class of a supramolecular complex for use as an anticancer agent, based on graft-polymerization onto a cationic derivative of a water-soluble linear backbone polymer. The cationic graft-copolymer of this invention is obtained by graft-polymerizing a vinyl monomer onto a cationic derivative of a water-soluble linear backbone polymer having hydroxyl groups. This specifically designed molecular structure of the Cationic graft-copolymer of this invention can react with Taxane-based anticancer agent to become a supramolecular complex by its hydrophobic bond etc. and ensures easy Taxane-based anticancer agent into cells via the cationic graft-copolymer-Taxane-based anticancer agent and endosome buffering.

Taxane is a generic name of diterpenes having a taxane ring expressed m formula (5) discovered in a plant of *Taxus* or its relation structure.

Taxane can be formed a supramolecular complex, reacted with the cationic graft-copolymer obtained by graft-polymerizing a vinyl monomer onto a cationic derivative of a water-soluble linear backbone polymer having hydroxyl groups. The kinds of taxane as below:

1. Taxadiene
    Taxadiene is a biochemical precursor for baccatin III or paclitaxel. In biosynthesis of *Taxus*, Taxadiene yield from Geranylgeranyl pyrophosphate, catalysed by taxadiene synthase.
2. Baccatin III
    Baccatin III compose of tetracyclic carbon-skelton by added oxetane ring to taxane ring, commonly in taxane anticancer agent.
    Baccatin III is used as precursor for docetaxel or paclitaxel synthesis because of easy to extract, it from *Taxus baccata*.
    10-deacetylbaccatins III is synthesized from 10-Deacetyl-2-debenzoylbaccatin III by 2-alpha-hydroxytaxane by 2-O-benzoyltransferase.
3. Paclitaxel
    Paclitaxel is discovered in the bark of *Taxus brevifolia*, it is used as an anticancer agent.
    Because it was not able to supply enough quantity as an anticancer agent, since only a very small quantity could be extracted from the yew tree and sufficient quantity as an anticancer agent was not able to be supplied, a synthetic method is studied actively, The half-synthetic method from 10-deacetylbaccatins III extracted from the needle leaf and sprig of the *Taxus baccata* tree was put in practical use, and the supply stable as an anticancer agent was attained.
4. Docetaxel
    The anticancer agent developed through screening of a compound with the anti-cancer activity of a paclitaxel family.
    The half-synthetic for docetaxel is accomplished from 10-deacetylbaccatins III extracted from the needle leaf and sprig of the *Taxus baccata* tree.
5. Taxchinin A
    Taxchinin A is a compound no having a tricyclic taxane ring of carbon number 6/8/6, but having a tricyclic Abeotaxane ring of carbon number 5/7/6.
    It is also called an Abeotaxane-diene ring or A-nortaxane ring. Taxchinin A is discovered from *Taxus chinensis*.
6. Brevifoliol
    The taxoid brevifoliol is found from *Taxus brevifolia*. Although it was thought that brevifoliol had a taxane ring, it has been identified that the brevifoliol actually has an Abeotaxane ring.
7. Taxuspine D
    It was discovered from the *Taxus cuspidata*.
    It differs from the existing anti-cancer agent taxane, although it has neither an oxetane ring considered to be important for the combination to a microtubule, nor a bulky side chain of the N-acyl-phenylisoserine group on the position of C-13 of a taxane ring, it has anti-cancer activity with a prevention action to microtubule de-polymerization like them.
    Moreover, it is known that its anti-cancer activity to the cancer cell which had medical treatment resistance in the existing taxoid anticancer agent by a functional prevention action from P-glycoprotein is important.
    Thus, unlike other anti-cancer agents, taxol is combined with the microtubule which constitutes a cytoskeleton. The action which inhibits cell division is shown, and attacking the prosperous cancer cell of cell division preferentially is suggested. As Paclitaxel for whole body administration, the medicine is manufactured in the mixture of the present ethanol and polyoxyethylated castor oil (Cremophor EL).
    Polyoxyethylated castor oil are the causes in which the allergic reaction relevant to a medicine more than the medicine itself.
    Docetaxel and paclitaxel are usually used 10-250 mg/m$^2$ (surface area of a body) per one time a day. Although a medicine is prescribed for the patient by intravenous drip infusion, reducing their side effects with the supramolecular complex of this invention is expected.

It was allowed encapsulated drugs such as anticancer drugs in polymeric micelles consisting of block copolymers having hydrophilic regions and hydrophobic regions, and encapsulation of paclitaxel in cationic liposomes.

These drug delivery using micelles are known as;
[PTL 2]
JP,2006-517594,A
[PTL 3]
JP,2001-226294,A
[PTL 4]
JP,2005-336402,A
[PTL 5]
JP,2007-023023,A These drugs delivery inhibit angiogenesis to endothelial cells of tumor blood vessels as a target charged anion and indicate the anti-tumor effect, but its reduce side effects is not complete. Recently, in vivo gene delivery has allowed the study of gene expression and function in animal models via insertion of foreign genes or alteration, of existing genes and/or their expression patterns. The clinical tests for transfection have become easy to carry out using a viral vector. But some dangerous adverse effects remain associated with the use of viral vectors.

Nonviral gene delivery vectors may be a key technology in circumventing the immunogenicity inherent in viral-mediated gene transfer.

Water-soluble cationic polysaccharides are also of interest for a nonviral gene delivery vector to increase safety by reducing the incidence of serious diseases resulting from the immunogenicity inherent in viral vectors.

When taxane is used instead of this nucleic acid using a complex with the cationic polymer body, taxane of a complex turns to it being send-able into the cell prepared beforehand directly. Although a cationic polysaccharide is promising as a polycation, because it is required for a complex to pass through a cell membrane, and this possibility originates in a positive charge of cationic polysaccharide and it is because of the cooperative reaction of an electric positive charge of complex with the electric negative charge on the surface of a cell membrane and the interaction of the polysaccharide on the surface of a cell membrane.

Biocompatible polymer is important for permeation selectivity of the cell membrane as a material for drug delivery system (DDS).

To give a more biocompatible property to material for DDS, its hydrophilic-hydrophobic micro domain is necessary.

It is important to use cationic polymer, specifically the cationic polysaccharides such as DEAE-dextran that form a latex comprising a copolymer of vinyl monomer onto it, and to have a hydrophilic portion by a cationic polysaccharide and a hydrophobic portion by polymerization of vinyl monomer.

It is also important this result for biocompatible latex complex with a hydrophilic-hydrophobic micro domain, but unexpectedly, supramolecular reaction with taxane to a copolymer of vinyl monomer and a cationic polysaccharide further increase by its structure, and it was discovered that it can improve the efficacy and the low rate of introduction of the taxane into the cells by DDS of cationic polysaccharides.

Advantageous Effects of Invention

This invention also provides a method of graft-polymerizing an olefin monomer onto a cationic derivative of a water-soluble linear polymer in water using ceric ammonium nitrate to obtain a stable and soap-less latex of the graft-copolymer.

This invention provides a novel graft-copolymer of formula (3) that is composed of a cationic derivative of a water-soluble linear polymer of formula (1) and a polymer of formula (2) by a vinyl monomer.

An intermediate complex between $Ce^{4+}$ ion and a hydroxyl group of the backbone polymer is formed and the oxidation-reduction proceeds via free radicals, capable of initiating vinyl polymerization. This invention obtain a stable and soap-less latex of the graft-copolymer. Namely, the obtained latex sensitized with an antibody or an antigen is agglutinated using an antigen or an antibody, and it can be confirmed rapidly whether the antigen or the antibody is present. The latex used for the L.A. (Latex Agglutination) test is typically a pure, stable and soapless substance and is also very effective as a non-viral gene delivery vector and a L.A. agent. The invention of U.S. Pat. No. 4,816,540 provides a novel graft-copolymer that is composed of a cationic derivative of a water-soluble linear polymer and an olefin monomer.

The invention described in U.S. Pat. No. 4,816,540 also provides a method of graft-polymerizing an olefin compound monomer onto a cationic derivative of a water-soluble linear polymer in water using ceric ammonium nitrate to obtain a stable and soap-less latex of the graft-copolymer.

Namely, the obtained latex sensitized with an antibody or an antigen is agglutinated using an antigen or an antibody, and it can be confirmed rapidly whether the antigen or the antibody is present. The latex used for the L.A. (Latex Agglutination) test is typically a pure, stable and soapless substance and is also very effective as a non-viral gene delivery vector.

It is shown in U.S. Pat. No. 3,989,656 that a dextran-alkyl methacrylate graft composition is obtained by polymerizing an olefin compound monomer onto a water-soluble linear polymer, such as dextran, in water using ceric ammonium nitrate.

The latex of the invention was effective for identification of an antigen or an antibody by antibody or antigen coating, namely, an immunoassay by analysis of the latex agglutination reaction. The novel latex of the invention was also useful as paint and a coating material due to its cationic properties.

This cationic graft-copolymer is thought to be useful as a micro carrier for cell cultivation and non-viral gene delivery vector.

As this cationic graft-copolymer has a hydrophilic-hydrophobic micro-separated domain to grow surfactant activity to cell surface, it is important for DDS to permeate cell membran. Supramolecule reaction this cationic graft-copolymer and taxane also grow up. Unexpected, this cationic graft-copolymer was found to be very promising as a material (DDS) drug delivery.

DESCRIPTION OF EMBODIMENTS

Figure 1:
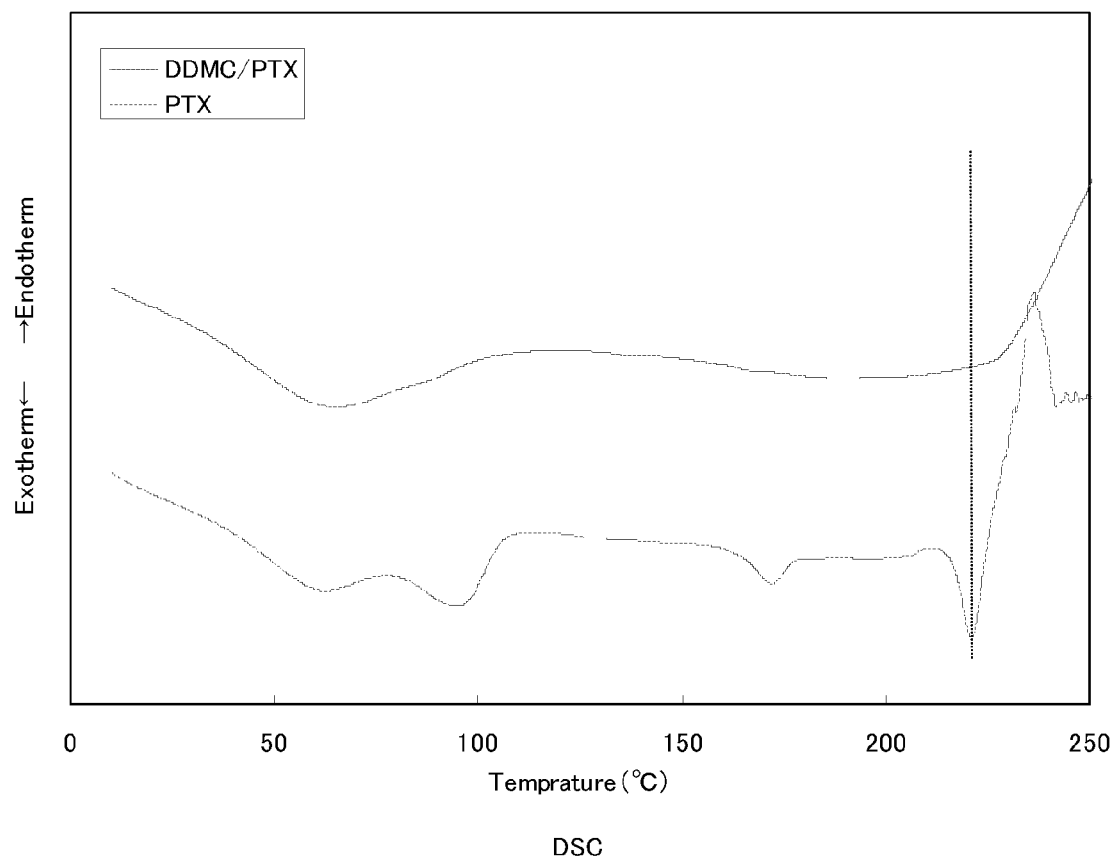
FIG. 1 is a diagram showing the Differential scanning calorimetry (DSC) curves of paclitaxel (PTX) and the complex by the DEAE(2-diethylaminoethyl)-dextran-methyl methacrylate graft copolymer (DDMC)/PTX (c) according to sample c of this invention.
Figure 2:
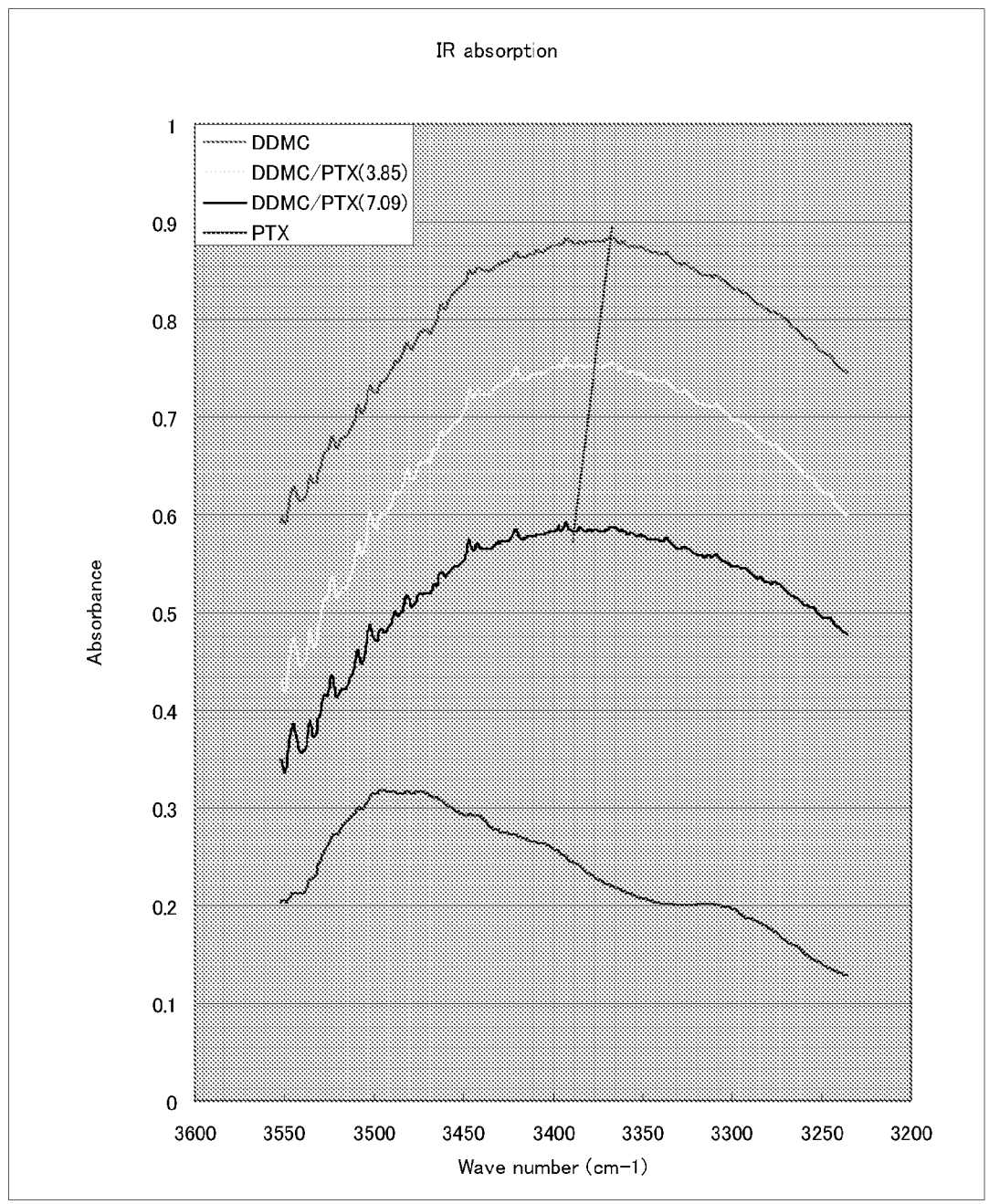
FIG. 2 is a diagram showing the infrared absorption spectra of the DEAE(2-diethylaminoethyl)-dextran-methyl methacrylate graft copolymer (DDMC) (grafting 102%), PTX and the complexes by DDMC/PTX (b)(c) according to sample b and c of this invention.
Figure 3:
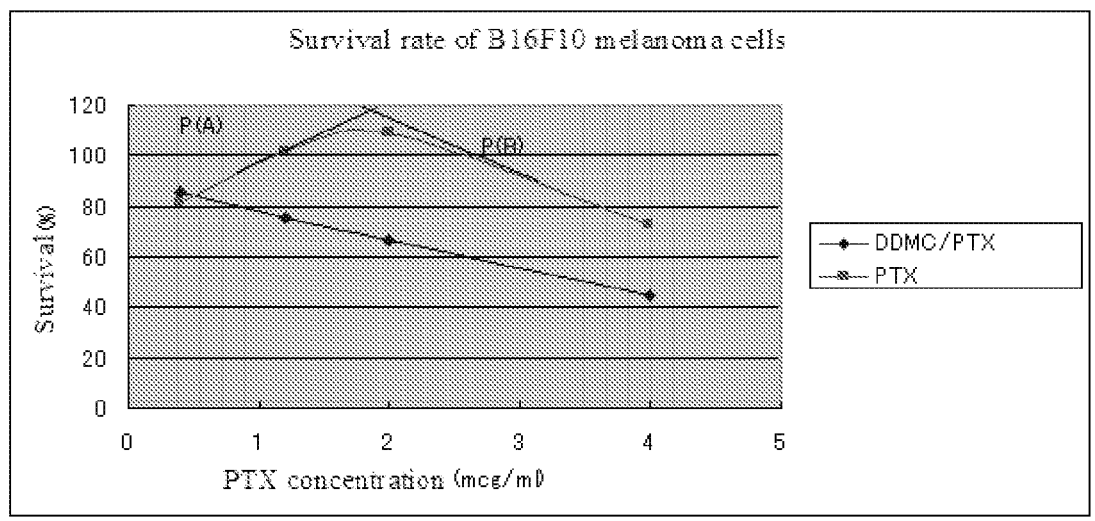
FIG. 3 is a diagram showing the Survival of B16F10 melanoma cells treated with paclitaxel or the DDMC-paclitaxel complex for 48 hours according to sample b of this invention.

The cationic copolymer of this invention can be produced by graft-polymerizing an olefin monomer onto a cationic derivative of a water-soluble linear polymer having hydroxyl groups using a red-ox initiator. The latex of the cationic graft-copolymer is obtained when the above-mentioned graft-polymerization is carried out in water via step (2) and step (3). The cationic copolymer of this invention can form supramolecular complex with anti-cancer drug, which make apoptosis.

(1) the Cationic Copolymer of this Invention

The cationic copolymer of this invention can be produced by graft-polymerizing an olefin compound monomer onto a cationic derivative of a water-soluble linear polymer having hydroxyl groups using a red-ox initiator. The latex of the cationic graft-copolymer is obtained when the above-mentioned graft-polymerization is carried out in water. Simple solid state polysaccharide cationic derivatives which are used here as a water-soluble linear polymer of this invention, such as dextran, pullulan, and dextrin, are comprised of a unit derived from a simple polysaccharide of formula (4).

$$(C_6H_7O_2(OH)_{3-a}(OX)_a)_x H_2O \quad (4)$$

Wherein X is a $—(CH_2)_m R_1$ organic radical where $R_1$ is a member of the class consisting of $—NH_2$ radical, $—N(CH_3)_2$ radical, $—N(C_2H_5)_2$ radical, $—N^+(C_2H_5)_3$ radical, $—N^+(CH_2)_2CH_2CH(OH)CH_3$ radical, $—N^+(C_2H_5)_2CH_2CH(OH)CH_3$ radical, $—N^+(C_2H_5)_2(C_2H_5)N(C_2H_5)_2$ radical, $—C_6H_4NH_2$ radical, and $—COC_6H_4NH_2$ radical, $—COR_2$ radical where $R_2$ is $—CH_2NH_2$ or $C_6H_4NH_2$, $—CH_2CH(OH)CH_2R_3$ radical where $R_3$ is $—NH_2$, $—N(CH_3)_2$, $—N(C_2H_5)_2$, and $—N^+(C_2H_5)_3$ radical, m is a natural number of 1 to 3, a is a positive number having a value of $0<a<3$, x is natural numbers having a value of 5 or more.

Other water-soluble linear polymers which are a water-soluble linear polymers having a hydroxyl groups can be used as starting materials besides the above-mentioned polymers. Examples of such other polymers are polyHEMA(2-hydroxyethyl methacrylate), the partial hydrolyzed polyvinyl acetates, and a water-soluble starch etc. These polymers have as a common property that each one is a water-soluble linear polymer having a hydroxyl groups, so that their hydroxyl groups can be easily replaced by the above-mentioned cationic groups reacting the chloride of the above-mentioned cationic group (XCl) with their hydroxyl group in the presence of alkali such as sodium hydroxide, potassium hydroxide, and sodium carbonate following. Schotten-Baumann Reaction and can easily form a alcohol red-ox system by red-ox initiators to polymerize olefin compound monomers onto them. Examples of such a red-ox initiator are a tetravalent ceric salt, a tetravalent manganese salt, and a ferric salt-hydrogenperoxide etc.

The polymerize-able olefin compound monomer is a compound which can form the recurring units shown in the parenthesis in the formula (2) upon polymerization.

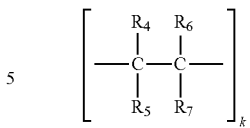

Wherein k is an integer of 10 to 200,000, $R_4$, $R_5$ and $R_6$ are each selected from the group consisting of hydrogen and $CH_3$ and $R_7$ is a member of the group consisting of

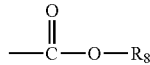

Where $R_8$ is a member of the class consisting of hydrogen, $C_1$-$C_{12}$ alkyl radicals, cyclohexyl radical, $C_1$-$C_4$ hydroxyalkyl radicals, $C_1$-$C_8$ aminoalkyl radicals, $C_1$-$C_8$ dialkylaminoalkyl radicals, glycidyl radical, tetrahydrofuran radical, $C_1$-$C_4$ lower alkyl-substituted tetrahydrofuran radical, benzyl radical, the $(CH_2CH_2O)_y CH_2CH_2OH$ radical where y is a positive integer from 1 to 10, and $—N(R_9)_2$ where the two $R_9$,s which may be the same or different, are either hydrogen or a $C_1$-$C_4$ alkyl radical;

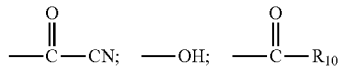

Where $R_{13}$ is a $C_1$-$C_8$ alkyl radical; phenyl radical; tolyl radical; pyridine radical; pyrrolidone radical; and

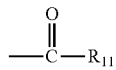

Where $R_{11}$ is $NH_2$ radical, $NHCH_3$ radical, N,N-dimethylamino radical, N,N-dimethylaminopropylamino radical, and morpholine radical.

As the polymerize-able olefin compound from which the unit expressed by the foregoing formula (2) is derived, there can be mentioned the alpha, beta-unsaturated acids such, for example, as acrylic acid and methacrylic acid; the alkyl esters of these alpha, beta-unsaturated acids; cyclohexyl ester or lower alkyl substituted cyclohexyl ester of the foregoing alpha, beta-unsaturated acids; the $C_1$-$C_4$ hydroxyalkyl esters of the alpha, beta-unsaturated acids such as the 2-hydroxyethyl esters, 2-hydroxypropyl ester and 2-hydroxybutyl ester of the foregoing alpha, beta-unsaturated acids; the amides or alkyl amides of the foregoing alpha, beta-unsaturated acids such as acrylamide, methacrylamide, acryl- or methacrylamide, acryl- or methacryl dimethylamide, acryl- or methacryl-N,N-dimethylaminopropylamide, acryl- or methacryl-morpholineamide; the $C_1$-$C_8$ aminoalkyl esters of the aforesaid alpha, beta-unsaturated acids; the $C_1$-$C_8$ dialkylaminoalkyl esters of the aforesaid alpha, beta-unsaturated acids; the glycidyl esters of the foregoing alpha, beta-unsaturated acids; the tetrahydrofurfuryl esters of the aforesaid alpha, beta-unsaturated acids; the benzyl esters of the foregoing alpha, beta-unsaturated acids; the polyethylene glycol monoesters such as the diethylene glycol, triethylene glycol and tetraethylene glycol monoesters of the aforesaid alpha, beta-unsaturated acids; the nitriles of the foregoing alpha, beta-unsaturated acids such as acrylonitrile and methacrylonitrile; vinyl alcohol, methylvinyl alcohol and dimethylvinyl alcohol; the $C_1$-$C_8$ alkyl esters of vinyl alcohol or the foregoing methyl-substituted vinyl alcohols such as vinyl acetate, vinyl propionate and vinyl butylate; styrene; alpha-methylstyrene and vinyl toluene; vinylpyridine; vinylpyrrolidone; and vinylmethylpyrrolidone.

(2) Preparation of the Cationic Copolymer

The cationic graft-copolymer of this invention consisting essentially of the water-soluble liner polymer cationic derivative units of the above formula (4) and the polymerized olefin compound units of the above formula (2) wherein k is an integer of 10 to 200,000 usually can be obtained by reacting the cationic derivative of the water-soluble linear polymer having a hydroxyl groups with a polymerize-able olefin monomer in the presence of a red-ox initiator in the absence of molecular oxygen in a water.

If desired, the use of the catalyst compound may be omitted, and the materials may be heat-polymerized under suspending or emulsifying conditions. Furthermore, it is also possible to polymerize the materials in solution by applying actinic radiation such as gamma-rays, X-rays, electron rays or ultraviolet rays.

Representative of red-ox initiators are a tetravalent cerium compounds. An intermediate complex between $Ce^{4+}$ ion and a hydroxyl group of the backbone polymer is formed and the oxidation-reduction proceeds via free radicals, capable of initiating vinyl polymerization. At this time, the presence of molecular oxygen reduces the activity of the red-ox initiator, and therefore, the reaction is desirably carried out after purging the reaction solution with nitrogen. The pH of the reaction system is not more than 6, preferably not more than 3 under acidic conditions. Examples of such a cerium compound are cerium ammonium nitrate, cerium sulfate, cerium ammonium sulfate, cerium nitrate, and cerium ammonium pyrophosphate. The reaction can be performed at room temperature, and temperature within a range of 0° C. to 80° C. are generally employed. When the initiator is utilized, the concentrations of the backbone polymer (the cationic derivative of the water-soluble linear polymer which is used in this invention), the polymerize-able olefin monomer and the initiator based on the total volume of the reaction system can be varied freely. For example, the preferred DEAE(2-diethylaminoethyl)-dextran hydrochloride concentration is 0.5 to 25 wt/vol %, the concentration of the methylmethacrylate 1 to 35 wt/vol %, and the cerium initiator concentration $5.5 \times 10^{-3}$ to $11 \times 10^{-1}$ mol/liter. The resulted latex of the cationic graft-copolymer can be purified to remove the residual monomer and the initiator by dialysis and reverse osmotic. Where the red-ox initiator is used, it may be deactivated after reaction by using a deactivating agent such as hydroquinone, sodium sulfate or ferrous sulfate. When a cationic graft-copolymer is wanted itself, the reaction product is precipitated using an alcohol. The by-product homopolymer may be removed with a suitable solvent such as acetone; tetrahydrofuran, dimethyl formamide, ethyl acetate or chloroform For the purpose mentioned above, the ratio of backbone polymer and grafted polymer or the degree of polymerization ratio owing to a purpose in a graft polymer in various ways can be chosen. As for the graft polymerization, a polymerization rate is determined in graft rate (%). This is defined with graft rate (%)=(graft-polymerized monomer weight/backbone polymer weight)×100. Olefin compounds become as a graft chain in this invention, and a graft rate (%) is thought suitable from 2% to 5,000%.

The present invention has been described repeatedly that this is obtained by graft polymerization of a monomer having an olefin under water onto a water soluble cationic derivative of linear polysaccharides having a hydroxyl group, the structure of the copolymer resulting of formula (3) is made of formula (1) and the formula (2) as has been described as a chemical formula in the claims,

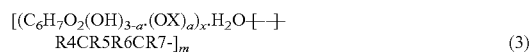

$$[(C_6H_7O_2(OH)_{3-a} \cdot (OX)_a)_x \cdot H_2O\{-\}- R4CR5R6CR7-]_m \quad (3)$$

Relationship of each bond is a covalent bond by the addition to the double bond of olefin monomer due to the occurrence of a radical by the withdrawal of the proton of the hydroxyl groups of the cationic derivative of linear water-soluble polysaccharides.

(3) Complex by Taxane/the Cationic Polysaccharide Graft-Copolymer

Delivery systems by the cationic polysaccharide copolymer of the present invention start from the first step of the formation of supramolecular complex consisting of both a taxane and a cationic polysaccharide copolymer of the present invention. For more information with the taxane delivery systems by the copolymer obtained by graft-polymerizing an olefin monomer onto a cationic partial replacement of the polysaccharide and linear polysaccharides, the formation of supramolecular complexes consisting of the taxane/the copolymer is an important first step.

Taxane is a generic name of diterpenes having a taxane ring expressed in formula (5) discovered in a plant of *Taxus* or its relation structure.

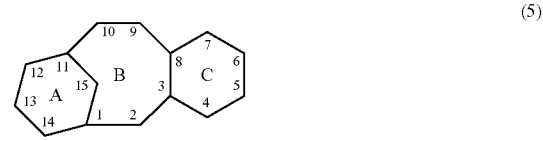

(5)

Where, number of carbon are 1-15, ring number are A, B, and C from C13 side.

Specifically, the paclitaxel:

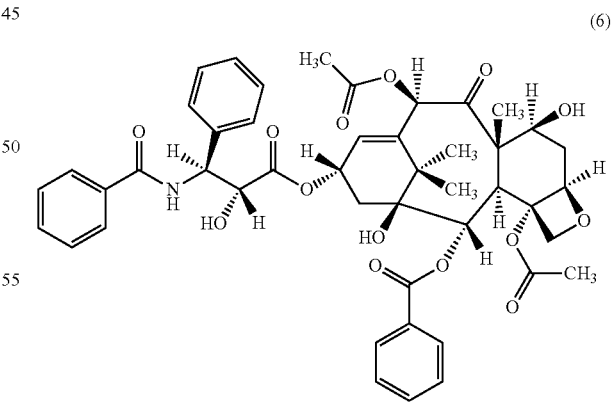

(6)

The complex between the cationic graft-copolymer of this invention and taxane, such as paclitaxel or docetaxel, consist essentially of the water-soluble liner polymer cationic derivative units of formulae (4), the polymerized olefin compound units of formula (2) upon polymerization, and taxane, such as paclitaxel or docetaxel, of formula (6) or (8).

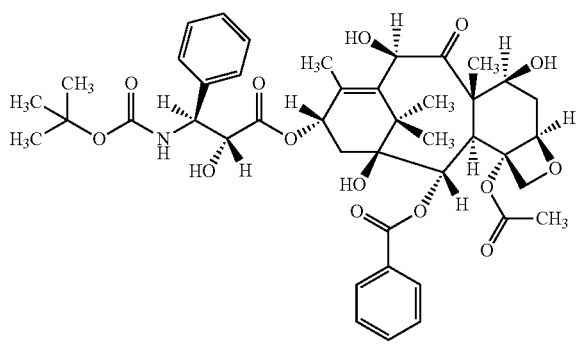

(8)

A hydrophobic moiety of taxane are shown in formula (6) or (8) is coupled to cationic polysaccharides by hydrophobic bond strength and it has been found cationic polysaccharide copolymer of the present invention can lead to complex with taxane. This supramolecular complex formation is an important first step of taxane delivery systems. Therefore, it is necessary to have a hydrophilic-hydrophobic domain for taxane cationic polymer delivery system.

The present invention provides a novel graft-copolymer for taxane cationic polymer delivery system that is composed of a cationic derivative of a water-soluble linear polymer and an olefin compound monomer.

The present invention also provides a method of graft-polymerizing an olefin monomer onto a cationic derivative of a water-soluble linear polymer in water using ceric ammonium nitrate to obtain a stable and soap-less latex of the graft-copolymer, which is very effective as taxane cationic polymer delivery system.

The specifically designed molecular structure of the cationic graft-copolymer having a hydrophilic-hydrophobic micro-separated-domain ensures easy entry of taxane into cells (i.e. transfection) by its cationic property or affinity to cell membrane, besides Enhanced Permeability and Retention (EPR) effects. The high efficiency of the graft-copolymer makes it a valuable tool for delivery system.

These drug delivery systems consist of an elementary step of formation of the complex between the cationic graft-copolymer so obtained and drug, such as paclitaxel or docetaxel. Preparation of a complex with a taxane and cationic polysaccharide copolymer can be obtained by dissolving the taxane to vinyl monomer during the polymerization reaction in advance and also be obtained by reacting directly taxane in the latex of cationic polysaccharides copolymer that arise.

By using the method of Example 2, paclitaxel(PTX) (a) 2.3 mg, (b) 7.7 mg, (c) 14.2 mg were clathrated in 10 ml of 19.2% aqueous solution of DEAE-dextran-MMA copolymer grafted at 100%, the resulted complex by DDMC/PTX (a), (b), and (c) were obtained. To investigate the physical properties of these products, thermal analysis and infrared analysis were carried out.

FIG. 1 shows the Differential scanning calorimetry (DSC) curves of paclitaxel (PTX) and the complex by DDMC/PTX (c). Here there are an endothermic peak (4) and one exothermic peak of the following three distinctive (1-3).

1 Elimination of non-structural water which are adsorbed on a sample (94.9° C.).

2 Dehydration from the paclitaxel dihydrate (171.8° C.)

3 The melting point of paclitaxel (220.8° C.) ΔHm=20.6 mJ/mg

4 Decomposition temperature (236° C.)

On the other hand, with the complex DDMC/PTX (a,b,c), the endothermic peak corresponding to the melting point of 220.8° C. did not appear in (a), (b) and (c). From this, it is considered that PTX has been the non-crystal at the inclusion in the complex by DDMC/PTX.

FIG. 2 shows infrared absorption spectrum of DDMC (grafting 102%), PTX and the complexes by DDMC/PTX (b) (c), which is near the wave number of 3200-3700 $cm^{-1}$.

The large absorptions of NH, OH, and NH—O, due to hydrogen bond by stretching vibration, are observed as more broad near 3400 $cm^{-1}$ with the complex by DDMC/PTX and DDMC, and in the vicinity of 3500 $cm^{-1}$ with PTX than the starting material, respectively.

Absorption of NH and OH has shifted further to higher energy side than the starting material, respectively.

This means that the association with the hydrogen bond itself is weakened, which then reassembled supramolecular hydrophobic complexes of them, DDMC by the binding of PTX is decreased the entropy than the state it is not bound. It is considered that the decrease is expected to be stable against a supramolecular stress. These things considered to be attributed to the conformational change happening in each of Supramolecule.

However, it has become the much larger when a change of shift to the high-energy side, of the absorption of the complex by DDMC/PTX.

The hydrophobic bond will be folded into three-dimensional structure by the driving force.

FIG. 2 shows more broad absorption by C—H stretching vibration near 3000 $cm^{-1}$ in the complex by DDMC/PTX compared with DDMC.

FIG. 2 shows the presence of a large hydrophobic binding in the complex by DDMC/PTX from the above.

A full-scale study of the enzyme was carried out by Dr. Willstatter, Germany (R. Willstatter), and from the purified saccharase the purified enzyme is thought to consist of active group of low molecular weight and high molecular weight carrier like saccharase (1920). Dr. Sumner from American (JBSumner) got the crystallized urease, and an enzyme was shown to be protein.

However, it is made possible by the large molecules of the enzyme protein.

What is thought to consist of low molecular weight active group and high molecular weight carrier is the original concept of Supramolecule.

MTT assay (direct method) has been found a positive correlation in between cell number and absorbance (the 0.D.), and MTT assay in vitro test is suitable as an efficacy evaluation of melanoma cells B16F10 to paclitaxel.

Resistance of melanoma cells B16F10 to paclitaxel has been shown in survival maximal curve like FIG. 3.

Survival curve, is convex to the concentration on PTX, which means to factor of gene expression in a concentration-dependent positive survival with PTX (A event) at low concentration and a negative factor for survival depending on the concentration of PTX (B event) at high concentrations, and it is considered to be due.

Where, the probability of survival is expressed by product event of probability, both P (A) positively and P(B) negatively, namely the product event A∩B where the probability of survival probability is the product event between the probability P (A) of the factor of gene expression survival depending positively at high concentration and the probability P (B) of the factor of gene expression survival depending negatively at high concentration.

Probability A∩B of this product event is the phenomenon that event A and B happen in event (A, B).

When event A and event B are independent each other, happening probability P(A∩B) of the product phenomenon is represented by a lower formula as;

$$P(A \cap B) = P(A) \cdot P(B)$$

P (A∩B): probability of event A and B
P (A): the probability of event A
P (B): the probability of event B Thus, it becomes the convex curve to assume P(A) and P(B) an asymptote.

Dr. S. Miyano of Tokyo University, he has researched the resistance to paclitaxel by melanoma cells (event A) to depend on survival rate plus to PTX density in a resistant study by DNA micro-array and dynamic Bayesian net work of Supercomputers, and it has been well described, by administering anti-cancer drug paclitaxel in melanoma cells, ie, onset of gene data measured in chronological order for 24 hours which gene cluster in an order appear for a time series of gene expression data in cells of melanoma.

Using the mathematics modeling of the dynamic Bayesian network method combined by non-linear regression method, it was calculated the super computer with $10^{24}$ cores and confirmed with DNA micro-array.

1 hour after the administration of paclitaxel, it became a major hub of RBM23 gene known to interact with the protein of Tubulin alpha-4A chain which is one of the target gene of paclitaxel-influence. Two hours after, TXNIP has become the hub known as a key gene that has been already not working for paclitaxel in breast cancer.

Four hours later, it came to see how the directives have come to a number of genes from EGR1 and TXNIP.

Six hours later, CYR61 which has been already known as a resistant gene of paclitaxel in breast cancer becomes more active. EGR1 continues affecting it, too. In this way, in the cancer cells which met with the crisis so-called the anticancer agent, it is said that their resistant change with time and show complex behaviors of cancer cell.

It is enough by the factor analysis of gene, expression in melanoma cells that positive survival will be depending on the low concentration of PTX in this experiment.

However, it is also hard to think that PTX does not participate in stabilization of Tubulin namely Tubulin polymerization at all even on the low concentration of PTX.

At high concentrations, however, superior to the negative survival factor depending on concentration PTX, it would come to promote a tubulin polymerization to be not able to inhibit more the expression of PTX.

Non-survival factor of concentration-dependent of PTX, (event B), becomes dominant, and the efficacy of PTX becomes remarkable.

On the other hand, the behavior of DDMC/PTX to melanoma cells is very specific. DDMC/PTX completely controls the increase of the melanoma cell from the low concentration, the behavior of DDMC/PTX are specific. Initial concentration of PTX $[E]_0$ and negative survival is dependent on a straight line.

In vivo analysis for melanoma cells is investigated by C57BL/6 female mouse. Anti-tumor effects and survival rates were investigated in tumor-bearing mice.

To evaluate the anti-tumor effects of DMMC/PTX complex, tumor-bearing mice were prepared by inoculating B16F10 melanoma cells S.C onto the back of C57BL/6 female mouse ($2.0 \times 10^6$ cells/mouse). At average 1885 mm³ of tumor volume, 12 days after inoculation, paclitaxel (PTX), DMMC/PTX4 (particle size 50 nm), DMMC/PTX5 (particle size 290 nm), and serine were administrated by I.P. injection three times (at a dose of 10 mg PXL/kg, on days 12, 14, and 16). Tumor size was measured with a digital vernier caliper and the volume was calculated using the relation V (mm³)= (a×b²)/2 where a is the longer, and b is the shorter diameter. The survival periods also monitored at 2 day intervals.

Anti-tumor effects and survival of tumor-bearing mice for supramolecular DDMC/PTX complex were very superior to PTX alone.

The tumor growth inhibitory activities were evaluated using B16F10 in xeno-graft tumor-bearing C57BL/6 mice. The tumors rapidly grew in size when the mice were treated with saline and PTX. But DDMC/PTX complex has more controlled to inhibit cancer growth than saline and PTX, and showed remarkable cancer growth inhibition after the 48 hours. The mean tumor volumes increase rate in the PTX, serine, DDMC/PTX4 and DDMC/PTX5 groups were 1.85, 1.84, 1.39 and 1.53, respectively.

The effects of the drugs, on the survival of tumor-bearing mice were also evaluated, and from the survival data summarized, the median survival times (50%, MST) of the serine, PTX, DDMC/PTX4 and DDMC/PTX5 groups were 120 hours (T/C, 1.0), 176 hours (T/C, 1.46), 352 hours (T/C, 2.93), and 292 hours (T/C, 2.43), respectively.

This means a valuable new discovery that it does not cause resistance of melanoma cells against complex by DDMC/PTX unexpectedly.

Following the procedure of Example 21, in the case of the hydrochloride salt of the DEAE(diethylaminoethyl)-dextran-MMA copolymer, five types of DEAE-dextran-MMA copolymer—paclitaxel complex have been prepared as the case 1, 2, 3, 4 and 5.

2 g of DEAE-dextran hydrochloride (nitrogen content 3%) derived from dextran having a weight average molecular weight of 500,000 was dissolved in 50 ml of water, and then total 7 ml by 2 ml of methyl methacrylate (MMA), in which contained 5 ml of the 25 mg, 50 mg, 75 mg, 100 mg, and 125 mg of paclitaxel dissolved by methanol were added as the case 1, 2, 3, 4 and 5. With stirring, the air in the reaction vessel was fully replaced with nitrogen gas. To the solution were added 0.1 g of ceric ammonium nitrate and 15 ml of 0.1N nitric acid, and the mixture was reacted with stirring for 2 hour at 30° C.

The reaction mixture was 3 ml of a 1% aqueous solution of hydroquinone, and then the resulted latex of DEAE-dextran-MMA copolymer was purified to remove the un-reacted MMA, eerie salts, and nitric acid to be done a water dialysis by using cellophane tube. The resulted latex of DEAE-dext-ran-MMA copolymer was stable and soap-less.

Paclitaxel was obtained carrying out measuring the absorbance of the 227 nm wavelength using a UV spectrophotometer to quantify the amount that is included in the paclitaxel micro-particle dispersion liquid.

The amounts of paclitaxel included in DDMC were 95%-98% (paclitaxel introduction rate) as Table 1.

TABLE 1

| | Paclitaxel introduction rate | | | | |
| --- | --- | --- | --- | --- | --- |
| | Sample | | | | |
| | case 1 | case 2 | case 3 | case 4 | case 5 |
| Inclusion (%) | 95 | 95 | 97 | 98 | 97 |

DSC analysis of the complex by DEAE-dextran-MMA copolymer(DDMC)/paclitaxel(PTX) of Example 2 was compared with A: PTX, and B: mixture of DDMC and PTX. The results are shown in Table 2.

The melting peak was seen near 224° C. with A: PTX, and B: mixture of DDMC and PTX, but the melting peak was not observed in the complex.

TABLE 2

DSC analysis

| | Sample | | |
|---|---|---|---|
| | A | B | C |
| Melting point (° C.) | 224 | 224 | — |

A: paclitaxel(PTX)
B: mixture of DDMC and PTX
C: complex by PTX/DDMC

Preparation of a complex between taxane and cationic polysaccharide copolymer can be obtained by dissolving a taxane in the vinyl monomer during the polymerization reaction in advance, excepting that it can also be obtained by reacting directly.

That is, paclitaxel (PTX) is dissolved in a solvent and is added drop-wise to a solution of 2% DEAE-dextran-MMA copolymer latex stirring this. The solution may be dispersed by ultrasonic wave. After continuing the agitation, a dialysis to remove un-reacted materials is performed in water to obtain a latex composite of complex by paclitaxel/DEAE-dextran-MMA copolymer. The filtration step may be added if desired and can use whatever PTX-soluble solvent, acetone, methanol, DMSO, dichloromethane, etc., or heating may be done while stirring a solvent herein.

Following the procedure in the case of example 1, the DEAE (diethylaminoethyl)-dextran-MMA copolymer on the three samples were prepared for a case 6, 7, and 8 respectively.

2 g of DEAE(2-diethylaminoethyl)-Dextran hydrochloride (nitrogen content 3%) derived from Dextran having a weight average molecular weight of 500,000 was dissolved in 50 ml of water, and then 3 ml, 4 ml, and 6 ml of methyl methacrylate (MMA) for case 6,7, and 8 respectively was added. With stirring, the air in the reaction vessel was fully replaced with nitrogen gas. To the solution were added 0.1 g of ceric ammonium nitrate and 15 ml of 0.1N nitric acid, and the mixture was reacted with stirring for 1 hour at 30° C. Then, 3 ml of a 1% aqueous solution of hydroquinone was added to stop the reaction, and then the resulted latex of DEAE-dextran-MMA copolymer was purified to remove the un-reacted MMA, ceric salts, and nitric acid to be done a water dialysis by using cellophane tube. The resulted latex of DEAE-dextran-MMA copolymer was stable and soap-less. This is very useful as a material for drug delivery, so that this can be reacted directly to the taxane.

Following the procedure in the case of example 2, by reacting a 3 mg of paclitaxel (PTX) (Taxol) respectively, Complex by PTX/DEAE-dextran-MMA copolymer of weight increase 100%, 150%, and 200% for case 6, case 7, and case 8 were obtained respectively. Introduction rate by each paclitaxel was about 90%. Here, the good fitting ratio of drugs/the polymer indicates from 100:1 to 200:30 when charged with a high stability of the aqueous solution of the complex.

Here, Weight increase (%)=(weight of MMA used/weight of DEAE-dextran hydrochloride used)×100

The kinds of Taxane have been used in the treatment of various tumors. Furthermore, there is not necessarily always effective because it is a substrate for P-GP which is a protein P-glycoprotein of multi-drug resistance. P-GP is said to be a drug transporter that pumped out of the cells. As inhibitor P-GP, valspodar, some of the calcium antagonist: verapamil, itraconazole and ketoconazole such as for antifungals. These is shown in rational formula $C_aH_bO_cN_d$ or $C_aH_bO_cN_d Cl_e$ where a, b, c, d, and e is natural number. We found that the combination of a P-GP inhibitors and Taxanes are useful there.

An inhibitor P-GP: valspodar

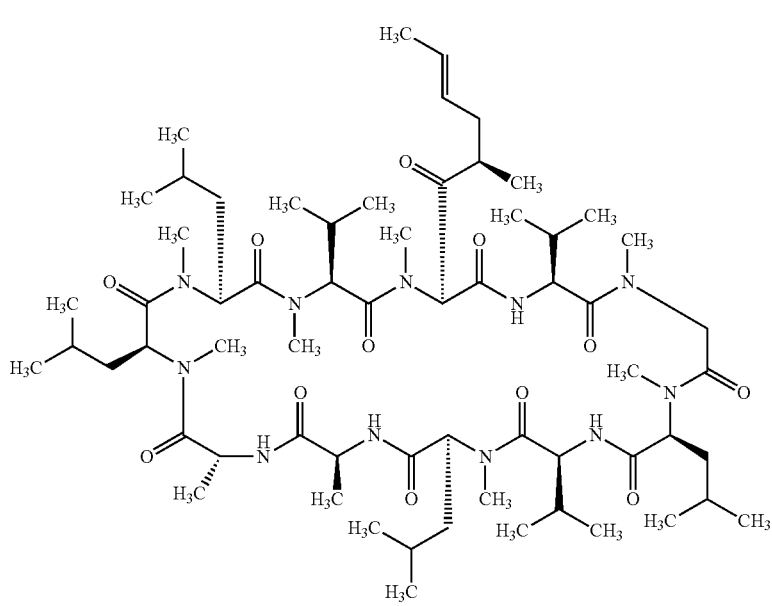

(7)

Barusupodaru as formula (7) made (referred valspodar, $C_{63}H_{111}N_{11}O_{12}$, PSC833 and thereafter).

The inclusion complex with hydrophobic bond in the molecule of DDMC can form as a complex DDMC/Barusupodaru/paclitaxel. Following the procedure of Example 2, DDMC reacting to a 3 mg of paclitaxel (PTX) is similar to the procedure, further to 1.5 mg PSC833 of P-glycoprotein (MDR1) inhibitor by dissolving in 2 ml of Dimethyl sulfoxide (DMSO) or acetone. Then dispersed well in the ultrasonic, after stirring was continued for 5 hours, to remove dimethyl sulfoxide or acetone, un-reacted mixture, and dialysis carried out in water.

The complexes by DDMC/Barusupodaru/PTX were obtained as case 8, case 9 and case 10 for DEAE-dextran-MMA copolymer of weight increase 100%, 150%, and 200%, respectively. Each paclitaxel introduction rate was around 90%, respectively.

TABLE 3

Paclitaxel introduction rate

| | Sample | | | | |
|---|---|---|---|---|---|
| case 6 | case 7 | case 8 | case 9 | case 10 | case 11 |
| Inclusion (%) 90 | 91 | 90 | 90 | 91 | 92 |

The results of DSC analysis show that a melting peak (° C.) did not exist, respectively.

TABLE 4

DSC analysis

| | Sample | | | | |
|---|---|---|---|---|---|
| case 6 | case 7 | case 8 | case 9 | case 10 | case 11 |
| Melting point (° C.) — | — | — | — | — | — |

These are also very useful as a drug delivery material.

It shows the results of MTT test using NIH/3T3 cell which established from the primary mouse embryonic fibroblast cells as shown in Table 5 and 6.

TABLE 5

MTT

| Sample | | | | | |
|---|---|---|---|---|---|
| Case 2 (DDMC only) | Case 2 | Case 6 (DDMC only) | Case 6 | Case 10 (DDMC only) | Case 10 |
| IC50 (μg/ml) — | 1.0 | — | 1.5 | — | 1.0 |

TABLE 6

MTT

| Sample | |
|---|---|
| control 1 | control 2 |
| IC50 (μg/ml) 3.0 | 4.5 |

(PTX)

Following procedure by MTT assay of DESCRIPTION OF EMBODIMENTS (4), after incubation of NIH/3T3 cells (mouse embryonic fibroblast cell line) for 50 hours at 37° C., cell viability was examined.

This test is a quantitative colorimetric method to determine cell proliferation. It utilizes the yellow tetrazolium salt [3-(4, 5-Dimethylthiazol-2-yl)-2,5-diphenyltetrazolium-bromide] which is metabolized by mitochondrial succinic dehydrogenase activity of proliferating cells to yield a purple formazan reaction product.

The formazan is then solubilized by isopropyl alcohol, and the concentration determined by optical density at 570 nm and cell survival was calculated using the following formula:

Cell survival (%)=((As−Ab)/(Ac−Ab))×100

Where, As=absorbance of the sample, Ac=absorbance of the control well (no cells) and Ab=absorbance of the blank well.

When you evaluate the cytotoxic $IC_{50}$ value (50% rate of cell injury) that the survival rate is 50%, as a result of comparing the samples of case 2 with the same amount of paclitaxel as control sample of the value of only one, three times the anti-cancer effect were obtained.

By the paclitaxel 30 mg by dissolving in absolute ethanol and 2.5 mL polyoxyethylene castor oil to total 5 mL, diluted with medium of MTT method to the amount of the same sample of case 2, it shows 3.0 of $IC_{50}$ (control 1) and 4.5 of $IC_{50}$ (control 2) value of only paclitaxel control of the same amount of sample of case 6. They also show three times the anti-cancer effect compared with control 1 and 2.

These can indicate that the cationic polysaccharide copolymer have a high reactivity with the cell.

The complex with these taxane is transmitted through the cell membrane, easily introduced into cells by the endosytosis, and is incorporated into the endosome (transport vesicle).

The complex further are released inside a cell from the endosome system, and integrated into the nucleus as a complex.

Taxane is separated from the complex in the nucleus, and usually facilitate cytostatic. These effects were not unexpected.

As supramolecule, one in some cytostatic taxanes is not separated in the nucleus for this purpose.

(4) MTT Test

1. Plate cells into 96-well tissue culture plates. Cells should be seeded at densities of 10,000 cells per well since they will reach optimal population densities within 24 to 48 hours.

2. Carry out the experiment by adding DDMC/PTX or PTX into appropriate well. The final volume of tissue culture medium in each well is 0.1 mL, and the medium may contain up to 10% Fetal Bovine Serum.

3. Use one vial of MTT solution for each 96-well plate assay.

4. Add 10 μL MTT solution to each well. Mix by tapping gently on the side of the tray or shake briefly on an orbital shaker.

5. Incubate at 37° C. for 2-4 hours.

6. Add 200 μL DMSO into each well to dissolve the formazan by pipetting up and down several times.

7. Read absorbance at 570 nm cell survival (%)=((As−Ab)/(Ac−Ab))×100

As: absorbance of sample
Ac: absorbance of no cells (control)
Ab: absorbance of blank Example 1

1 g of DEAE(2-diethylaminoethyl)-dextran hydrochloride (nitrogen content 5%) derived from dextran having a weight average molecular weight of 500,000 was dissolved in 30 ml. of water, and then 2 ml. of methyl methacrylate (MMA) was added. With stirring, the air in the reaction vessel was fully replaced with nitrogen gas. To the solution were added 0.1 g of ceric ammonium nitrate and 7.5 ml. of 0.1N nitric acid, and the mixture was reacted with stirring for 2 hour at 30° C. Then, 3 ml. of a 1% aqueous solution of hydroquinone was added to stop the reaction. The reaction mixture was poured into methanol to form a precipitate. The precipitate formed was washed with hot water, centrifuged, and dried at 50° C. under reduced pressure. The crude DEAE-dextran-MMA copolymer so obtained was placed in a Soxhlet extractor, and extracted for 24 hours continuously using acetone, to afford 2.0 g of a purified DEAE-dextran-MMA copolymer. The yield was 80% in DEAE-dextran, the nitrogen content was 2.0%, and the grafting (%) was 150%. The grafting (%) is expressed by the following equation.

Grafting (%)=(weight of MMA graft-polymerized/ weight of DEAE-dextran hydrochloride in the copolymer)×100

The resulted DEAE-dextran-MMA copolymer is insoluble in water and acetone at 25° C. In view of the fact that DEAE-dextran hydrochloride is soluble in water and poly(MMA) is soluble in acetone, it is evident that the DEAE-dextran-MMA copolymer is not a mixture of DEAE-dextran and poly (MMA).

The infrared absorption spectrum of the copolymer has, some characteristic absorption bands at 1730 $cm^{-1}$ and at 1000 to 1150 $cm^{-1}$, which is attributed to the carbonyl group of poly(MMA) and the pyranose ring of DEAE-dextran, respectively. Thus, the resulting DEAE-dextran-MMA copolymer exhibits different solubility from DEAE-dextran and poly(MMA) and shows the above-described characteristic absorption in infrared absorption spectrum. From this fact, it is judged that the resulting DEAE-dextran-MMA copolymer is a compound graft-polymerized.

Example 2

The procedure of Example 1 was repeated till stopping the reaction by adding 3 ml. of a 1% aqueous solution of hydroquinone, and then the resulted latex of DEAE-dextran-MMA copolymer was purified to remove the un-reacted MMA, ceric salts, and nitric acid to be done a water dialysis by using cellophane tube. The resulted latex of DEAE-dextran-MMA copolymer was stable and soap-less.

3 mg of paclitaxel (Taxol) (PTX) dissolved in 2 ml acetone was added dropwise to 10 ml of 2% solution of the DEAE-dextran-MMA copolymer latex with agitation. Then, the solution was continued stirring for 5 hours after dispersing well by ultrasonic, to remove acetone and un-reacted substances, and was carried out dialysis in water, we obtain a latex composite of complex by paclitaxel/DEAE-dextran-MMA copolymer.

Paclitaxel introduction rate was 90% from the UV absorbance of the 227 nm wavelength.

Example 3

Composite latex of complex by paclitaxel/DEAE-dextran-MMA copolymer of Example 2 is useful as a material of drug delivery system (DDS). Following procedure by MTT assay of DESCRIPTION OF EMBODIMENTS (4), after incubation of MDA-MB-231 cells (human breast cancer cell line) for 50 hours at 37° C., the cell viability $IC_{50}$ (μg/ml) was examined. The effect of anti-cancer by DDS was due to cytotoxicity by $IC_{50}$ (μg/ml). The result of comparing the same amount of sample of Example 2, as a value of 1 for only paclitaxel (Taxol) control, was obtained as increased anti-cancer effects of three times, namely $IC_{50}$ values are $\frac{1}{3}$.

Example 4

A latex of the complex by DEAE-dextran-MMA copolymer(DDMC)/paclitaxel(PTX) obtained in Example 2 was freeze-dried, and DSC analysis of the complex was compared with paclitaxel(PTX), the melting peak was seen near 224° C. with PTX, but the melting peak was not observed in the complex.

Example 5

Procedure of Example 1 was repeated, except that 4 g of DEAE(2-diethylaminoethyl)-pullulan hydrochloride (nitrogen content 4%) derived from a pullulan having a weight average molecular weight of 200,000, 80 ml. of water, 35 ml. of purified styrene monomer, 10 ml. of methanol, 30 ml. of 0.1N nitric acid, 0.2 g of ceric ammonium nitrate, and tetrahydrofuran for a Soxhlet extract were used, to afford 6 g of a purified DEAE-pullulan-styrene copolymer. The yield was 38% in DEAE-pullulan, the nitrogen content was 0.92%, and the grafting (%) was 350%. The resulted DEAE-pullulan-styrene copolymer is insoluble in water and tetrahydrofuran.

Example 6

The procedure of Example 2 was repeated with DEAE-pullulan-styrene copolymer of Example 5 to result the latex of DEAE-pullulan-styrene copolymer. According to the procedure of Example 2, 3 mg of paclitaxel (Taxol) (PTX) dissolved in 2 ml acetone was added drop-wise to 10 ml of 2% solution of the DEAE-pullulan-styrene copolymer latex with agitation. Then, the solution was continued stirring for 5 hours after dispersing well by ultrasonic, to remove acetone and un-reacted substances, and was carried out dialysis in water, we obtain a latex composite of complex by paclitaxel/DEAE-pullulan-styrene copolymer. Paclitaxel introduction rate was 91% from the UV absorbance of the 227 nm wavelength.

Example 7

Composite latex of complex by paclitaxel/DEAE-pullulan-styrene copolymer of Example 6 is useful as a material of drug delivery system (DDS).

The procedure of Example 3 was repeated with complex by paclitaxel/DEAE-pullulan-styrene copolymer of Example 6, The anti-cancer effect by DDS was due to cytotoxicity by $IC_{50}$ (μg/ml). The result of comparing the same amount of sample of Example 6, as a value of 1 for only paclitaxel (Taxol) control, was obtained as increased anti-cancer effects of 2.5 times ($IC_{50}$ values are $\frac{2}{5}$).

Example 8

A latex of the complex by DEAE-pullulan-styrene copolymer/paclitaxel (PTX) obtained in Example 6 was freeze-dried, and DSC analysis of the complex was compared with paclitaxel (PTX). The melting peak was seen near 224° C. with PTX, but the melting peak was not observed in the complex:

Example 9

Example 1 was repeated, except that 4 g of AE(aminoethyl)-dextran hydrochloride (nitrogen content 5%) derived from dextran having a weight average molecular weight of 40,000, 90 ml. of water, 20 ml. of butyl methacrylate (BMA), and 0.05 g of ceric ammonium nitrate, to afford 6 g of a purified AE-dextran-BMA copolymer. The yield was 38% in AE-dextran, the nitrogen content was 1.3%, and the grafting (%) was 300%. The resulted AE-dextran-BMA copolymer is insoluble in water and acetone.

Example 10

The procedure of Example 2 was repeated with AE-dextran-BMA copolymer of Example 9 to result the latex of AE-dextran-BMA copolymer. According to the procedure of Example 2, 3 mg of paclitaxel (Taxol) (PTX) dissolved in 2 ml acetone was added drop-wise to 10 ml of 2% solution of the AE-dextran-BMA copolymer latex with agitation. Then, the solution was continued stirring for 5 hours after dispersing well by ultrasonic, to remove acetone and un-reacted substances, and was carried out dialysis in water, we obtain a latex composite of complex by paclitaxel/AE-dextran-BMA copolymer.

Paclitaxel introduction rate was 90% from the UV absorbance of the 227 nm wavelength.

Example 11

Composite latex of complex by paclitaxel/AE-dextran-BMA copolymer of Example 10 is useful as a material of drug delivery system (DDS).

The procedure of Example 3 was repeated with paclitaxel/AE-dextran-BMA copolymer of Example 10, the effects of anti-cancer by DDS was due to cytotoxicity by $IC_{50}$ (µg/ml). The result of comparing the same amount of sample of Example 10, as a value of 1 for only paclitaxel (Taxol) control, was obtained as increased anti-cancer effects of 2.0 times ($IC_{50}$ values are ½).

Example 12

A latex of the complex by AE-dextran-BMA copolymer/paclitaxel (PTX) obtained in Example 10 was freeze-dried, and DSC analysis of the complex was compared with paclitaxel (PTX). The melting peak was seen near 224° C. with PTX, but the melting peak was not observed in the complex.

Example 13

Example 1 was repeated, except that 4 g of HPTMA(2-hydroxypropyltrimethylammonium)-pullulan hydrochloride (nitrogen content 3%) derived from pullulan having a weight average molecular weight of 30,000, 100 ml. of water, 30 ml. of methyl acrylate (MA), 20 ml. of 0.1N nitric acid, 0.2 g of ceric ammonium nitrate, 4 ml. of a 1% aqueous solution of hydroquinone, to afford 2 g of a purified HPTMA-pullulan-MA copolymer.

The yield was 20% in HPTMA-pullulan, the nitrogen content was 1.2%, and the grafting (%) was 150%. The resulted HPTMA-pullulan-MA copolymer is insoluble in water and acetone.

Example 14

The procedure of Example 2 was repeated with HPTMA-pullulan-MA copolymer of Example 13 to result the latex of HPTMA-pullulan-MA copolymer. According to the procedure of Example 2, 3 mg of paclitaxel (Taxol) (PTX) dissolved in 2 ml acetone was added drop-wise to 10 ml of 2% solution of the HPTMA-pullulan-MA copolymer latex with agitation. Then, the solution was continued stirring for 5 hours after dispersing well by ultrasonic, to remove acetone and un-reacted substances, by carried out dialysis in water, we obtain a latex composite of complex by paclitaxel/HPTMA-pullulan-MA copolymer.

Paclitaxel introduction rate was 92% from the UV absorbance of the 227 nm wavelength.

Example 15

Composite latex of complex by paclitaxel/HPTMA-pullulan-MA copolymer of Example 14 is useful as a material of drug delivery system (DDS).

The procedure of Example 3 was repeated with paclitaxel/HPTMA-pullulan-MA copolymer of Example 14, The effects of anti-cancer by DDS was due to cyto-toxicity by $IC_{50}$ (µg/ml). The result of comparing the same amount of sample of Example 14, as a value of 1 for only paclitaxel (Taxol) control, was obtained as increased anti-cancer effects of 2.1 times ($IC_{50}$ values are 10/21).

Example 16

A latex of the complex by paclitaxel/HPTMA-pullulan-MA copolymer obtained in Example 14 was freeze-dried, and DSC analysis of the complex was compared with paclitaxel (PTX). The melting peak was seen near 224° C. with PTX, but the melting peak was not observed in the complex.

Example 17

2 g of TEAE(triethylaminoethyl)-dextran hydrochloride (nitrogen content 2%) derived from dextran having a weight average molecular weight of 300,000 was dissolved in 50 ml. of water, and then 15 ml. of methyl acrylate (MA) was added. With stirring, the air in the reaction vessel was fully replaced with nitrogen gas. To the solution were added 0.25 g of ceric ammonium nitrate and 15 ml. of 0.1N nitric acid, and the mixture was reacted with stirring for hours at 30° C. Then, 3 ml. of a 1% aqueous solution of hydroquinone was added to stop the reaction. The reaction mixture was poured into methanol to form a precipitate. The precipitate formed was washed with hot water, centrifuged, and dried at 50° C. under reduced pressure. The crude TEAE-dextran-MA copolymer so obtained was placed in a Soxhlet extractor, and extracted for 24 hours continuously using acetone, to afford 2.0 g of a purified TEAE-dextran-MA copolymer. The yield was 35% in TEAE-dextran, the nitrogen content was 0.7%, and the grafting (%) was 185%. The grafting (%) is expressed by the following equation.

Grafting (%)=(weight of MA graft-polymerized/
weight of TEAE-dextran hydrochloride in the
copolymer)×100

The resulted TEAE-dextran-MA copolymer is insoluble in water and acetone at 25° C. In view of the fact that TEAE-dextran hydrochloride is soluble in water and poly(MA) is soluble in acetone, it is evident that the TEAE-dextran-MA copolymer is not a mixture of TEAE-dextran and poly(MA).

Example 18

The procedure of Example 2 was repeated with TEAE-dextran-MA copolymer of Example 17 to result the latex of TEAE-dextran-MA copolymer. According to the procedure of Example 2, 3 mg of paclitaxel (Taxol) (PTX) dissolved in 2 ml acetone was added drop-wise to 10 ml of 2% solution of the TEAE-dextran-MA copolymer latex with agitation. Then, the solution was continued stirring for 5 hours after dispersing well by ultrasonic, to remove acetone and un-reacted substances, by carried out dialysis in water, we obtain a latex composite of complex by paclitaxel/TEAE-dextran-MA copolymer.

Paclitaxel introduction rate was 90% from the UV absorbance of the 227 nm wavelength.

Example 19

Composite latex of complex by paclitaxel/TEAE-dextran-MA copolymer of Example 18 is useful as a material of drug delivery system (DDS).

The procedure of Example 3 was repeated with paclitaxel/TEAE-dextran-MA copolymer of Example 18, The effects of anti-cancer by DDS was due to cytotoxicity by $IC_{50}$ (μg/ml). The result of comparing the same amount of sample of Example 18, as a value of 1 for only paclitaxel (Taxol) control, was obtained as increased anti-cancer effects of 3.0 times ($IC_{50}$ values are 1/3).

Example 20

A latex of the complex by paclitaxel/HTEAE-dextran-MA copolymer obtained in Example 18 was freeze-dried, and DSC analysis of the complex was compared with paclitaxel (PTX). The melting peak was seen near 224° C. with PTX, but the melting peak was not observed in the complex.

Example 21

1 g of DEAE(2-diethylaminoethyl)-dextran hydrochloride (nitrogen content 5%) derived from dextran having a weight average molecular weight of 500,000 was dissolved in 30 ml. of water, then 2 ml. of methyl methacrylate (MMA) and 0.05 g of paclitaxel (PTX) dissoluble in methanol 5 ml. were added. With stirring, the air in the reaction vessel was fully replaced with nitrogen gas. To the solution were added 0.1 g of ceric ammonium nitrate and 2.5 ml. of 0.1N nitric acid, and the mixture was reacted with stirring for 2 hours at 30° C. Then, 3 ml. of a 1% aqueous solution of hydroquinone was added to stop the reaction. The reaction mixture was poured into methanol to form a precipitate. The precipitate formed was washed with hot water, centrifuged, and dried at 50° C. under reduced pressure. The crude complex by PTX/DEAE-dextran-MMA copolymer so obtained was placed in a Soxhlet extractor, and extracted for 24 hours continuously using acetone, to afford 5.0 g of a purified complex by PTX/DEAE-dextran-MMA copolymer. The yield of DEAE-dextran was 50%, the nitrogen content was 1.7%, and the grafting (%) was 200%.

The resulted complex by PTX/DEAE-dextran-MMA copolymer is insoluble in water and acetone at 25° C. In view of the fact that DEAE-dextran hydrochloride is soluble in water and poly(MMA) is soluble in acetone, it is evident that the complex by PTX/DEAE-dextran-MMA copolymer is not a mixture of DEAE-dextran, PTX, and poly(MMA).

The infrared absorption spectrum of the copolymer has some characteristic absorption bands at 1730 $cm^{-1}$ and at 1000 to 1150 $cm^{-1}$, which is attributed to the carbonyl group of poly(MMA) and the pyranose ring of DEAE-dextran, respectively.

Example 22

The procedure of Example 21 was repeated till stopping the reaction by adding 3 ml. of a 1% aqueous solution of hydroquinone, and then the resulted latex of complex by PTX/DEAE-dextran-MMA was purified to remove the unreacted MMA, ceric salts, and nitric acid to be done a water dialysis by using cellophane tube. The resulted latex of complex by PTX/DEAE-dextran-MMA was stable.

Paclitaxel introduction rate was 90% from the UV absorbance of the 227 nm wavelength.

Example 23

Composite latex of complex by paclitaxel/DEAE-dextran-MMA copolymer of Example 22 is useful as a material of drug delivery system (DDS).

Following procedure by MTT assay of DESCRIPTION OF EMBODIMENTS (4), after incubation of MDA-MB-231 cells (human breast cancer cell line) for 50 hours at 37° C., the cell viability $IC_{50}$ (g/ml) was examined. The effect of anti-cancer by DDS was due to cytotoxicity by $IC_{50}$ (μg/ml). The result of comparing the same amount of sample of Example 22, as a value of 1 for only paclitaxel (Taxol) control, was obtained as increased anti-cancer effects of 3.5 times, namely IC50 values are 2/7.

Example 24

A latex of the complex by paclitaxel/DEAE-dextran-MMA copolymer obtained in Example 22 was freeze-dried, and DSC analysis of the complex was compared with paclitaxel (PTX). The melting peak was seen near 224° C. with PTX, but the melting peak was not observed in the complex.

Example 25

Example 21 was repeated except docetaxel (DOC/TXT) and 1.4 g of the complex by docetaxel/DEAE-dextran-MMA copolymer was obtained. The yield was 45% in DEAE-dextran, the nitrogen content was 1.61%, and the grafting (%) was 210%. The resulted the complex by docetaxel/DEAE-dextran-MMA copolymer is insoluble in water and acetone at 25° C. The infrared absorption spectrum of the copolymer has some characteristic absorption bands at 1730 $cm^{-1}$ and at 1000 to 1150 $cm^{-1}$, which is attributed to the carbonyl group of poly(MMA) and the pyranose ring of DEAE-dextran, respectively.

Example 26

Examples 22 was repeated except docetaxel (DOC/TXT) and the complex by docetaxel/DEAE-dextran-MMA copolymer was obtained.

Docetaxel introduction rate was 90% from the UV absorbance of the 228 nm wavelength.

Example 27

Composite latex of complex by docetaxel/DEAE-dextran-MMA copolymer of Example 26 is useful as a material of drug delivery system (DDS).

Following procedure by MTT assay of DESCRIPTION OF EMBODIMENTS (4), after incubation of MDA-MB-231 cells (human breast cancer cell line) for 72 hours at 37° C., the cell viability $IC_{50}$ (μg/ml) was examined. The effect of anti-cancer by DDS was due to cytotoxicity by $IC_{50}$ (μg/ml). The result of comparing the same amount of sample of Example 26, as a value of 1 for only docetaxel control, was obtained as increased anti-cancer effects of 3.4 times, namely $IC_{50}$ values are 5/17.

Example 28

The latex of the complex by docetaxel/DEAE-dextran-MMA copolymer obtained in Example 26 was freeze-dried, and DSC analysis of the complex was compared with docetaxel. The melting peak was seen near 230° C. with docetaxel alone, but the melting peak was not observed in the complex.

Example 29

The procedure of Example 2 was repeated with DEAE-dextran-MMA copolymer to result the latex of the complex by paclitaxel/DEAE-dextran-MMA having 250% weight increase. According to the procedure of Example 2, 1.5 mg of Valspodar (PSC833) dissolved in 2 ml DMSO was added drop-wise to 10 ml of 2% solution of the latex of the complex by paclitaxel/DEAE-dextran-MMA with agitation. Then, the solution was continued stirring for 5 hours after dispersing well by ultrasonic, to remove DMSO and un-reacted substances, by carried out dialysis in water, we obtain a latex composite of the complex by paclitaxel/PSC833/DEAE-dextran-MMA copolymer.

Paclitaxel introduction rate was 90% from the UV absorbance of the 227 nm wavelength.

Composite latex of the complex by paclitaxel/PSC833/DEAE-dextran-MMA copolymer of Example 29 is useful as a material of drug delivery system (DDS).

Following procedure by MTT assay of DESCRIPTION OF EMBODIMENTS (4), after incubation of MDA-MB-231 cells (human breast cancer cell line) for 72 hours at 37° C., the cell viability $IC_{50}$ (µg/ml) was examined. The effect of anticancer by DDS was due to cytotoxicity by $IC_{50}$ (µg/ml). The result of comparing the same amount of sample of Example 29, as a value of 1 for only paclitaxel control, was obtained as increased anti-cancer effects of 3.0 times, namely $IC_{50}$ values are ⅓.

Weight increase (%)=weight of MMA graft-polymerized/weight of DEAE-dextran Hydrochloride in the copolymer)×100

INDUSTRIAL APPLICABILITY

The cationic copolymers of this invention have superior properties for a material of drug delivery system (DDS), when compared with other DDS material owing to their industrially applicable properties, such as inexpensive price, biological safety, stability, and the ability to mass produce them.

Due to their stability, it is possible to autoclave at 120° C. for 15 minutes for sterilization. These properties are suitable for industrial production.

What is claimed is:

1. A complex between a cationic graft-copolymer of a water-soluble linear backbone polymer having hydroxyl groups and Taxane by hydrophobic bond, comprising a unit derived from a cationic water-soluble linear polysaccharide of the following formula (1)

$$(C_6H_7O_2(OH)_{3-a}(OX)_a)_x H_2O \quad (1)$$

Wherein X is a $-(CH_2)_m R_1$ organic radical where $R_1$ is a member of the class consisting of $-NH_2$ radical, $-N(CH_3)_2$ radical, $-N(C_2H_5)_2$ radical, $-N^+(C_2H_5)_3$ radical, $-N^+(CH_2)_2CH_2CH(OH)CH_3$ radical, $-N^+(C_2H_5)_2CH_2CH(OH)CH_3$ radical, $-N^+(C_2H_5)_2(C_2H_5)N(C_2H_5)_2$ radical, $-C_6H_4NH_2$ radical, and $-COC_6H_4NH_2$ radical, $-COR_2$ radical where $R_2$ is $-CH_2NH_2$ or $-C_6H_4NH_2$, $-CH_2CH(OH)CH_2R_3$ radical where $R_3$ is $-NH_2$, $-N(CH_3)_2$, $-N(C_2H_5)_2$, and $-N^+(C_2H_5)_3$ radical, m is a natural number of 1 to 3, a is a positive number having a value of 0<a<3, x is natural numbers having a value of 5 or more; a unit derived from a polymerize-able olefin compound of the following formula (2)

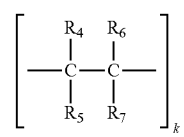

(2)

Wherein k is an integer of 10 to 200,000, $R_4$, $R_5$ and $R_6$ are each selected from the group consisting of hydrogen and $CH_3$, and $R_7$ is a member of the group consisting of

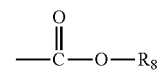

Where $R_8$ is a member of the class consisting of hydrogen, $C_1$-$C_{12}$ alkyl radicals, cyclohexyl radical, $C_1$-$C_4$ hydroxyalkyl radicals, $C_1$-$C_8$ aminoalkyl radicals, $C_1$-$C_8$ dialkylaminoalkyl radicals, glycidyl radical, tetrahydrofuran radical, $C_1$-$C_4$ lower alkyl-substituted tetrahydrofuran radical, benzyl radical, the $(CH_2CH_2O)_y$ $CH_2CH_2OH$ radical where y is a positive integer from 1 to 10, and $-N(R_9)_2$ where the two $R_9$,s which may be the same or different, are either hydrogen or a $C_1$-$C_4$ alkyl radical;

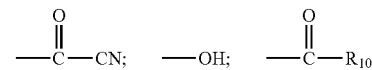

Where $R_{10}$ is a $C_1$-$C_8$ alkyl radical; phenyl radical; tolyl radical; pyridine radical; pyrrolidone radical; and

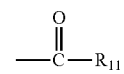

Where $R_{11}$ is $NH_2$, $NHCH_3$, N,N-dimethylamino radical, N,N-dimethylaminopropylamino radical, and morpholine radical; and a unit derived from Taxane of the following formula (5)

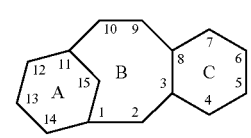

(5)

Where, number of carbon are 1-15, ring number are A, B, and C from C13 side.

2. A complex between a cationic graft-copolymer of a water-soluble linear backbone polymer having hydroxyl groups, Taxane and P-glycoprotein (P-gp) inhibitor by hydrophobic bond, comprising a unit derived from a cationic water-soluble linear polysaccharide of the following formula (1)

Wherein X is a —$(CH_2)_m R_1$ organic radical where $R_1$ is a member of the class consisting of —$NH_2$ radical, —$N(CH_3)_2$ radical, —$N(C_2H_5)_2$ radical, —$N^+(C_2H_5)_3$ radical, —$N^+(CH_2)_2CH_2CH(OH)CH_3$ radical, —$N^+(C_2H_5)_2CH_2CH(OH)CH_3$ radical, —$N^+(C_2H_5)_2(C_2H_5)N(C_2H_5)_2$ radical, —$C_6H_4NH_2$ radical, and —$COC_6H_4NH_2$ radical, —$COR_2$ radical where $R_2$ is —$CH_2NH_2$ or —$C_6H_4NH_2$, —$CH_2CH(OH)CH_2R_3$ radical where $R_3$ is —$NH_2$, —$N(CH_3)_2$, —$N(C_2H_5)_2$, and —$N^+(C_2H_5)_3$ radical, m is a natural number of 1 to 3, a is a positive number having a value of 0<a<3, x is natural numbers having a value of 5 or more; a unit derived from a polymerize-able olefin compound of the following formula (2)

Wherein k is an integer of 10 to 200,000, $R_4$, $R_5$ and $R_6$ are each selected from the group consisting of hydrogen and $CH_3$, and $R_7$ is a member of the group consisting of

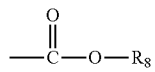

Where $R_8$ is a member of the class consisting of hydrogen, $C_1$-$C_{12}$ alkyl radicals, cyclohexyl radical, $C_1$-$C_4$ hydroxyalkyl radicals, $C_1$-$C_8$ aminoalkyl radicals, $C_1$-$C_8$ dialkylaminoalkyl radicals, glycidyl radical, tetrahydrofuran radical, $C_1$-$C_4$ lower alkyl-substituted tetrahydrofuran radical, benzyl radical, the $(CH_2CH_2O)_y CH_2CH_2OH$ radical where y is a positive integer from 1 to 10, and —$N(R_9)_2$ where the two $R_9$,s which may be the same or different, are either hydrogen or a $C_1$-$C_4$ alkyl radical;

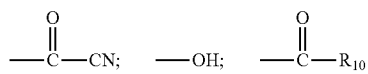

Where $R_{10}$ is a $C_1$-$C_8$ alkyl radical; phenyl radical; tolyl radical; pyridine radical; pyrrolidone radical; and

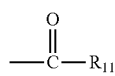

Where $R_{11}$ is $NH_2$, $NHCH_3$, N,N-dimethylamino radical, N,N-dimethylaminopropylamino radical, and morpholine radical; and a unit derived from Taxane of the following formula (5) and a unit selected from the group of P-GP inhibitor shown in rational formula $C_a H_b O_c N_d$ or $C_a H_b O_c N_d Cl_e$ where a, b, c, d, and e is natural number

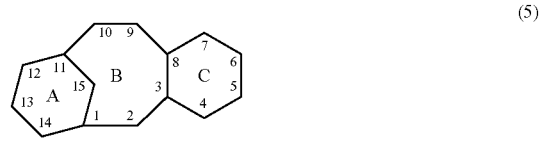

Where, number of carbon are 1-15, ring number are A, B, and C from C13 side.

3. A complex between a cationic graft-copolymer of a water-soluble linear backbone polymer having hydroxyl groups and paclitaxel by hydrophobic bond, comprising a unit derived from a cationic water-soluble linear polysaccharide of the following formula (1)

Wherein X is a —$(CH_2)_m R_1$ organic radical where $R_1$ is a member of the class consisting of —$NH_2$ radical, —$N(CH_3)_2$ radical, —$N(C_2H_5)_2$ radical, —$N^+(C_2H_5)_3$ radical, —$N^+(CH_2)_2CH_2CH(OH)CH_3$ radical, —$N^+(C_2H_5)_2CH_2CH(OH)CH_3$ radical, —$N^+(C_2H_5)_2(C_2H_5)N(C_2H_5)_2$ radical, —$C_6H_4NH_2$ radical, and —$COC_6H_4NH_2$ radical, —$COR_2$ radical where $R_2$ is —$CH_2NH_2$ or —$C_6H_4NH_2$, —$CH_2CH(OH)CH_2R_3$ radical where $R_3$ is —$NH_2$, —$N(CH_3)_2$, —$N(C_2H_5)_2$, and —$N^+(C_2H_5)_3$ radical, m is a natural number of 1 to 3, a is a positive number having a value of 0<a<3, x is natural numbers having a value of 5 or more; a unit derived from a polymerize-able olefin compound of the following formula (2)

Wherein k is an integer of 10 to 200,000, $R_4$, $R_5$ and $R_6$ are each selected from the group consisting of hydrogen and $CH_3$, and $R_7$ is a member of the group consisting of

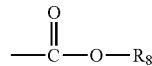

Where $R_8$ is a member of the class consisting of hydrogen, $C_1$-$C_{12}$ alkyl radicals, cyclohexyl radical, $C_1$-$C_4$ hydroxyalkyl radicals, $C_1$-$C_8$ aminoalkyl radicals, $C_1$-$C_8$ dialkylaminoalkyl radicals, glycidyl radical, tetrahydrofuran radical, $C_1$-$C_4$ lower alkyl-substituted tetrahydrofuran radical, benzyl radical, the $(CH_2CH_2O)_y CH_2CH_2OH$ radical where y is a positive integer from 1 to 10, and —$N(R_9)_2$ where the two $R_9$,s which may be the same or different, are either hydrogen or a $C_1$-$C_4$ alkyl radical;

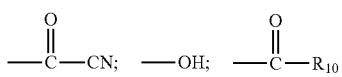

Where $R_{10}$ is a $C_1$-$C_8$ alkyl radical; phenyl radical; tolyl radical; pyridine radical; pyrrolidone radical; and

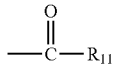

Where $R_{11}$ is $NH_2$, $NHCH_3$, N,N-dimethylamino radical, N,N-dimethylaminopropylamino radical, and morpholine radical; and a unit derived from paclitaxel of the following formula (6)

(6)

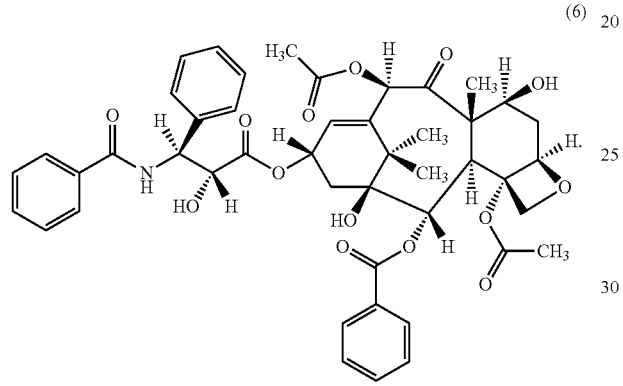

4. A complex between a cationic graft-copolymer of a water-soluble linear backbone polymer having hydroxyl groups, Taxane and valspodar by hydrophobic bond, comprising a unit derived from a cationic water-soluble linear polysaccharide of the following formula (1)

(1)

Wherein X is a —$(CH_2)_m R_1$ organic radical where $R_1$ is a member of the class consisting of —$NH_2$ radical, —$N(CH_3)_2$ radical, —$N(C_2H_5)_2$ radical, —$N^+(C_2H_5)_3$ radical, —$N^+(CH_2)_2CH_2CH(OH)CH_3$ radical, —$N^+(C_2H_5)_2CH_2CH(OH)CH_3$ radical, —$N^+(C_2H_5)_2(C_2H_5)N(C_2H_5)_2$ radical, —$C_6H_4NH_2$ radical, and —$COC_6H_4NH_2$ radical, —$COR_2$ radical where $R_2$ is —$CH_2NH_2$ or —$C_6H_4NH_2$, —$CH_2CH(OH)CH_2R_3$ radical where $R_3$ is —$NH_2$, —$N(CH_3)_2$, —$N(C_2H_5)_2$, and —$N^+(C_2H_5)_3$ radical, m is a natural number of 1 to 3, a is a positive number having a value of 0<a<3, x is natural numbers having a value of 5 or more; a unit derived from a polymerize-able olefin compound of the following formula (2)

(2)

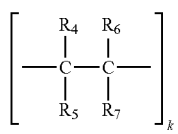

Wherein k is an integer of 10 to 200,000, $R_4$, $R_5$ and $R_6$ are each selected from the group consisting of hydrogen and $CH_3$, and $R_7$ is a member of the group consisting of

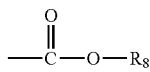

Where $R_8$ is a member of the class consisting of hydrogen, $C_1$-$C_{12}$ alkyl radicals, cyclohexyl radical, $C_1$-$C_4$ hydroxyalkyl radicals, $C_1$-$C_8$ aminoalkyl radicals, $C_1$-$C_8$ dialkylaminoalkyl radicals, glycidyl radical, tetrahydrofuran radical, $C_1$-$C_4$ lower alkyl-substituted tetrahydrofuran radical, benzyl radical, the $(CH_2CH_2O)_y$ $CH_2CH_2OH$ radical where y is a positive integer from 1 to 10, and —$N(R_9)_2$ where the two $R_9$,s which may be the same or different, are either hydrogen or a $C_1$-$C_4$ alkyl radical;

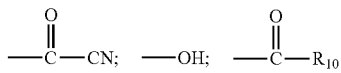

Where $R_{10}$ is a $C_1$-$C_8$ alkyl radical; phenyl radical; tolyl radical; pyridine radical; pyrrolidone radical; and

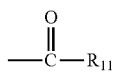

Where $R_{11}$ is $NH_2$, $NHCH_3$, N,N-dimethylamino radical, N,N-dimethylaminopropylamino radical, and morpholine radical; a unit derived from paclitaxel of the following formula (6);

(6)

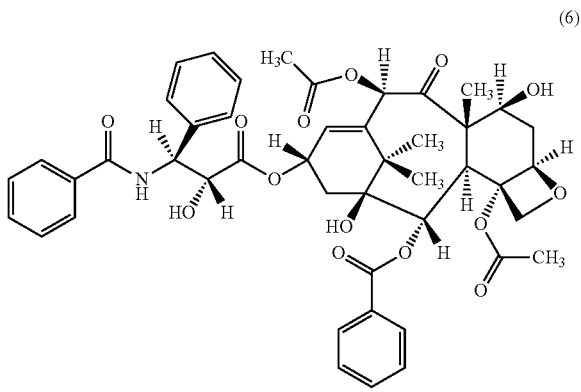

and a unit derived from valspodar of the following formula (7).

(7)

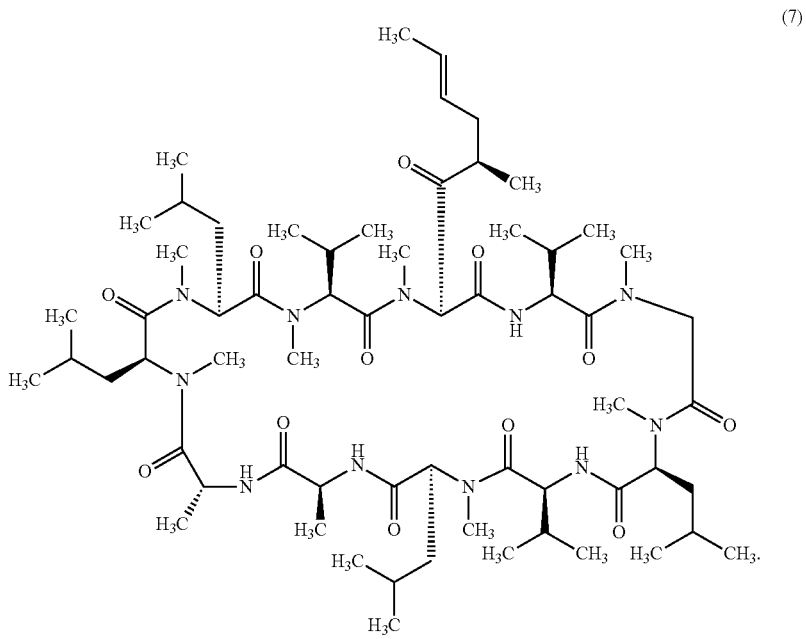 [SMILES: C/C=C/C[C@@H](C)C(=O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

5. A complex between a cationic graft-copolymer of a water-soluble linear backbone polymer having hydroxyl groups and docetaxel by hydrophobic bond, comprising a unit derived from a cationic water-soluble linear polysaccharide of the following formula (1)

$$(C_6H_7O_2(OH)_{3-a}(OX)_a)_x H_2O \quad (1)$$

Wherein X is a $-(CH_2)_m R_1$ organic radical where $R_1$ is a member of the class consisting of $-NH_2$ radical, $-N(CH_3)_2$ radical, $-N(C_2H_5)_2$ radical, $-N^+(C_2H_5)_3$ radical, $-N^+(C_2H_5)_2CH_2CH(OH)CH_3$ radical, $-N^+(C_2H_5)_2CH_2CH(OH)CH_3$ radical, $-N^+(C_2H_5)_2(C_2H_5)N(C_2H_5)_2$ radical, $-C_6H_4NH_2$ radical, and $-COC_6H_4NH_2$ radical, $-COR_2$ radical where $R_2$ is $-CH_2NH_2$ or $-C_6H_4NH_2$, $-CH_2CH(OH)CH_2R_3$ radical where $R_3$ is $-NH_2$, $-N(CH_3)_2$, $-N(C_2H_5)_2$, and $-N^+(C_2H_5)_3$ radical, m is a natural number of 1 to 3, a is a positive number having a value of 0<a<3, x is natural numbers having a value of 5 or more; a unit derived from a polymerize-able olefin compound of the following formula (2)

(2)

Wherein k is an integer of 10 to 200,000, $R_4$, $R_5$ and $R_6$ are each selected from the group consisting of hydrogen and $CH_3$, and $R_7$ is a member of the group consisting of

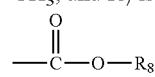

Where $R_8$ is a member of the class consisting of hydrogen, $C_1$-$C_{12}$ alkyl radicals, cyclohexyl radical, $C_1$-$C_4$ hydroxyalkyl radicals, $C_1$-$C_8$ aminoalkyl radicals, $C_1$-$C_8$ dialkylaminoalkyl radicals, glycidyl radical, tet- rahydrofuran radical, $C_1$-$C_4$ lower alkyl-substituted tetrahydrofuran radical, benzyl radical, the $(CH_2CH_2O)_y CH_2CH_2OH$ radical where y is a positive integer from 1 to 10, and $-N(R_9)_2$ where the two $R_9$,s which may be the same or different, are either hydrogen or a $C_1$-$C_4$ alkyl radical;

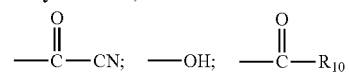

Where $R_{10}$ is a $C_1$-$C_8$ alkyl radical; phenyl radical; tolyl radical; pyridine radical; pyrrolidone radical; and

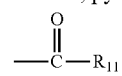

Where $R_{11}$ is $NH_2$, $NHCH_3$, N,N-dimethylamino radical, N,N-dimethylaminopropylamino radical, and morpholine radical; and a unit derived from docetaxel of the following formula (8)

(8)

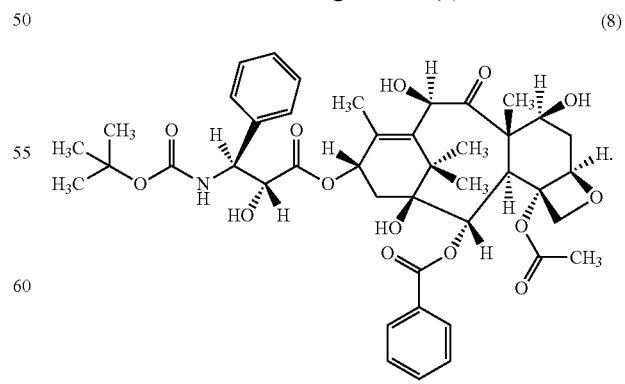

6. A Drug Delivery System using a complex between a cationic graft-copolymer and Taxane, of claim 1.

7. A Drug Delivery System using a complex between a cationic graft-copolymer, Taxane, and P-glycoprotein (P-gp) inhibitor, of claim 2.

8. A Drug Delivery System using a complex between a cationic graft-copolymer and paclitaxel, of claim 3.

9. A Drug Delivery System using a complex between a cationic graft-copolymer, paclitaxel and valspodar, of claim 4.

10. A Drug Delivery System using a complex between a cationic graft-copolymer and docetaxel, of claim 5.

* * * * *